(12) United States Patent
Makarova et al.

(10) Patent No.: US 11,613,115 B2
(45) Date of Patent: Mar. 28, 2023

(54) POLYMER MICROFILTERS AND METHODS OF MANUFACTURING THE SAME

(75) Inventors: Olga V. Makarova, Potomac, MD (US); Cha-Mei Tang, Potomac, MD (US); Platte T Amstutz, Potomac, MD (US)

(73) Assignee: CREATV MICROTECH, INC., Potomac, MD (US)

( * ) Notice: Subject to any disclaimer, the term of this patent is extended or adjusted under 35 U.S.C. 154(b) by 166 days.

(21) Appl. No.: 13/696,139

(22) PCT Filed: Apr. 1, 2011

(86) PCT No.: PCT/US2011/030966
§ 371 (c)(1),
(2), (4) Date: Nov. 5, 2012

(87) PCT Pub. No.: WO2011/139445
PCT Pub. Date: Nov. 10, 2011

(65) Prior Publication Data
US 2013/0059308 A1    Mar. 7, 2013

Related U.S. Application Data

(60) Provisional application No. 61/377,797, filed on Aug. 27, 2010, provisional application No. 61/330,819, filed on May 3, 2010.

(51) Int. Cl.
*G01N 1/40*    (2006.01)
*G01N 33/50*   (2006.01)
(Continued)

(52) U.S. Cl.
CPC .......... *B41F 33/0081* (2013.01); *B01D 29/00* (2013.01); *B01D 39/16* (2013.01);
(Continued)

(58) Field of Classification Search
CPC .......... B01L 3/5027; B01L 3/502; B01L 3/50; C12M 25/02; B01D 2325/028;
(Continued)

(56) References Cited

U.S. PATENT DOCUMENTS 4,454,749 A    6/1984 Guillemin et al.
4,783,318 A    11/1988 Lapakko
(Continued)

FOREIGN PATENT DOCUMENTS

CN    1767898 A    5/2006
EP    1031371 A1   8/2000
(Continued)

OTHER PUBLICATIONS

Kanikella, PR.2007 "Process development and applications of a dry film photoresist" Masters Theses. 6821. https://scholarsmine.mst.edu/masters_theses/6821 (Year: 2007).*
(Continued)

*Primary Examiner* — Liam Royce
(74) *Attorney, Agent, or Firm* — Dickinson Wright PLLC

(57) ABSTRACT

A microfilter comprising a polymer layer formed from epoxy-based photo-definable dry film, and a plurality of apertures each extending through the polymer layer. A method of forming a microfilter is also disclosed. The method includes providing a first layer of epoxy-based photo-definable dry film disposed on a substrate, exposing the first layer to energy through a mask to form a pattern, defined by the mask, in the first layer of dry film, forming, from the exposed first layer of dry film, a polymer layer having a plurality of apertures extending therethrough, the plurality of apertures having a distribution defined by the pattern, and removing the polymer layer from the substrate.

20 Claims, 24 Drawing Sheets

(51) Int. Cl.
*B01L 3/00* (2006.01)
*B01D 29/00* (2006.01)
*B01D 39/16* (2006.01)
*B01D 71/46* (2006.01)
*B01L 9/00* (2006.01)
*B41F 33/00* (2006.01)
*B31B 50/00* (2017.01)
*B31B 100/00* (2017.01)
*B31B 50/88* (2017.01)

(52) U.S. Cl.
CPC ......... *B01D 39/1692* (2013.01); *B01D 71/46* (2013.01); *B01L 3/50* (2013.01); *B01L 3/5635* (2013.01); *B01L 9/00* (2013.01); *B41F 33/0036* (2013.01); *G01N 1/4005* (2013.01); *G01N 1/4077* (2013.01); *G01N 33/5005* (2013.01); *B01D 2239/0421* (2013.01); *B01D 2239/10* (2013.01); *B01L 3/502* (2013.01); *B01L 2300/0681* (2013.01); *B31B 50/006* (2017.08); *B31B 50/88* (2017.08); *B31B 2100/0022* (2017.08); *G01N 2001/4088* (2013.01); *Y10T 29/49826* (2015.01); *Y10T 29/49963* (2015.01)

(58) Field of Classification Search
CPC ............ B01D 2325/02; B01D 2325/08; B01D 2325/12; B01D 67/0034; B01D 67/0032; B01D 67/0023; B01D 67/0002; B01D 67/0088; B01D 67/0081; B01D 71/46; B01D 71/06; B01D 61/14; B01D 71/022; B01D 71/02; B01D 71/72; B01D 61/18; B01D 2325/021; B01D 29/002; B01D 29/03; B01D 39/1692; G03F 7/038; G03F 7/004; G03F 7/0385; G03F 7/161; G03F 7/16; G03F 7/0015
See application file for complete search history.

(56) References Cited

U.S. PATENT DOCUMENTS

| | | | |
|---|---|---|---|
| 5,221,483 | A | 6/1993 | Glenn et al. |
| 5,807,406 | A * | 9/1998 | Brauker .................. A61F 2/00 424/422 |
| 5,932,100 | A | 8/1999 | Yager et al. |
| 6,241,886 | B1 | 6/2001 | Kitagawa et al. |
| 6,346,192 | B2 | 2/2002 | Buhr et al. |
| 6,716,568 | B1 * | 4/2004 | Minsek ................. G03F 7/0382 430/272.1 |
| 2002/0041827 | A1 | 4/2002 | Yager et al. |
| 2002/0094303 | A1 | 7/2002 | Yamamoto et al. |
| 2002/0122918 | A1 | 9/2002 | Dentinger et al. |
| 2003/0138941 | A1 * | 7/2003 | Gong .................... B01L 3/5027 435/287.2 |
| 2003/0180807 | A1 | 9/2003 | Hess et al. |
| 2004/0036751 | A1 | 2/2004 | Giere et al. |
| 2004/0131957 | A1 | 7/2004 | Kubota et al. |
| 2004/0182788 | A1 | 9/2004 | Dorian et al. |
| 2005/0073600 | A1 | 4/2005 | Sato |
| 2005/0266335 | A1 | 12/2005 | Johnson et al. |
| 2006/0124865 | A1 | 6/2006 | Wolfe et al. |
| 2006/0133766 | A1 | 6/2006 | Shelnut et al. |
| 2007/0025883 | A1 | 2/2007 | Tai et al. |
| 2008/0023572 | A1 | 1/2008 | Clark |
| 2008/0063802 | A1 | 3/2008 | Maula et al. |
| 2008/0164155 | A1 | 7/2008 | Pease et al. |
| 2008/0299695 | A1 | 12/2008 | Ouellet et al. |
| 2009/0042736 | A1 | 2/2009 | Bomer et al. |
| 2009/0073400 | A1 | 3/2009 | Wolfe et al. |
| 2009/0202813 | A1 | 8/2009 | Itami et al. |
| 2009/0258791 | A1 | 10/2009 | McDevitt et al. |
| 2009/0321964 | A1 * | 12/2009 | Summerfelt ........ H01L 23/3135 257/787 |
| 2010/0038303 | A1 | 2/2010 | Cai et al. |

FOREIGN PATENT DOCUMENTS

| | | |
|---|---|---|
| GB | 2392854 A | 3/2004 |
| JP | 58-68899 U | 5/1983 |
| WO | 9513860 A1 | 5/1995 |
| WO | 2008086477 A1 | 7/2008 |
| WO | 2010/085337 | 7/2010 |

OTHER PUBLICATIONS

International Search Report for International Application No. PCT/US11/30966 dated Aug. 17, 2011 (5 pages).
Written Opinion for International Application No. PCT/US11/30966 dated Aug. 17, 2011 (8 pages).
P Abgrall et al., "Lab-on-chip technologies: making a microfluidic network and coupling it into a complete microsystem—a review", Journal of Micromechanics and Microengineering 17 (2007) R15-R49 (35 pages).
Rebecca J Jackman et al., "Microfluidic systems with on-line UV detection fabricated in photodefinable epoxy", Journal of Micromechanics and Microengineering 11 (2001) 263-269 (7 pages)>.
DuPont(TM) PerMX(TM) 3000 Photodielectric Dry Film Adhesive Technical Data Sheet.
EMS Inc. Technical Data Sheet, DF-1014, Negative I-Line Dry Film Photoresist.
DuPont(TM) PerMX(TM) 3000 Photodielectric Dry Film Adhesive Technical Data Sheet, 2010.
EMS Inc. Technical Data Sheet, DF-1014, Negative l-Line Dry Film Photoresist, 2009.

* cited by examiner

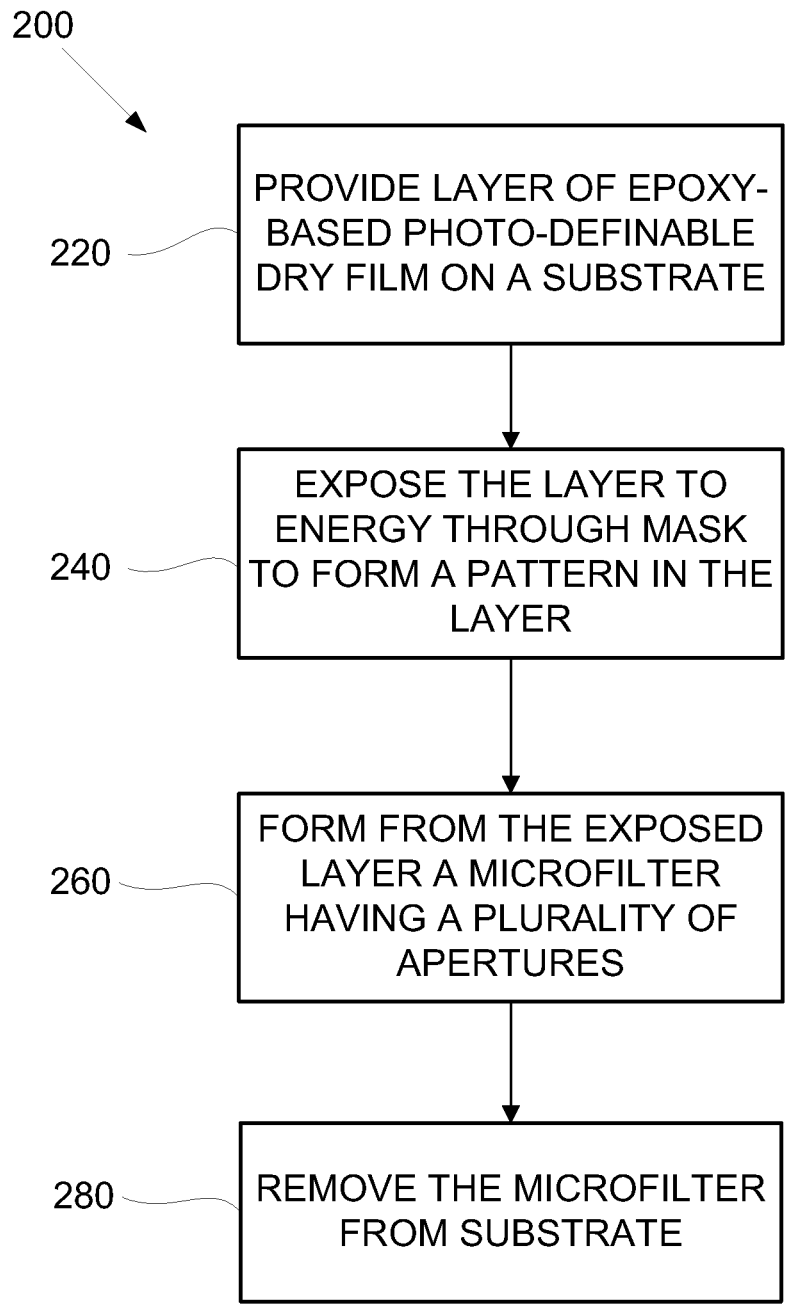

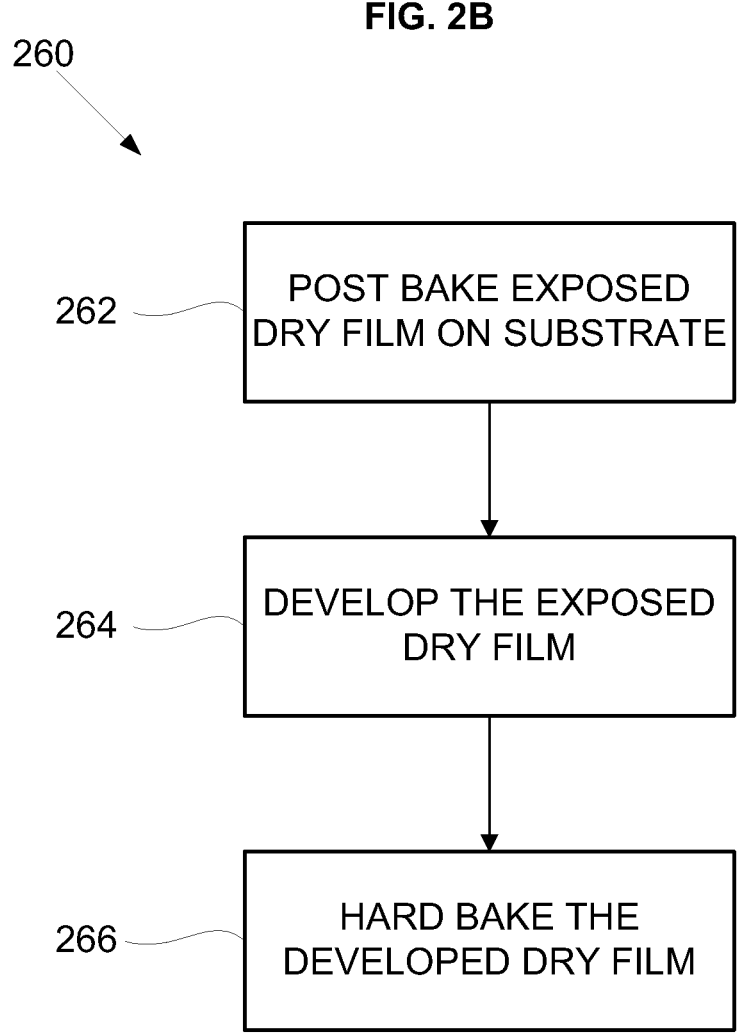

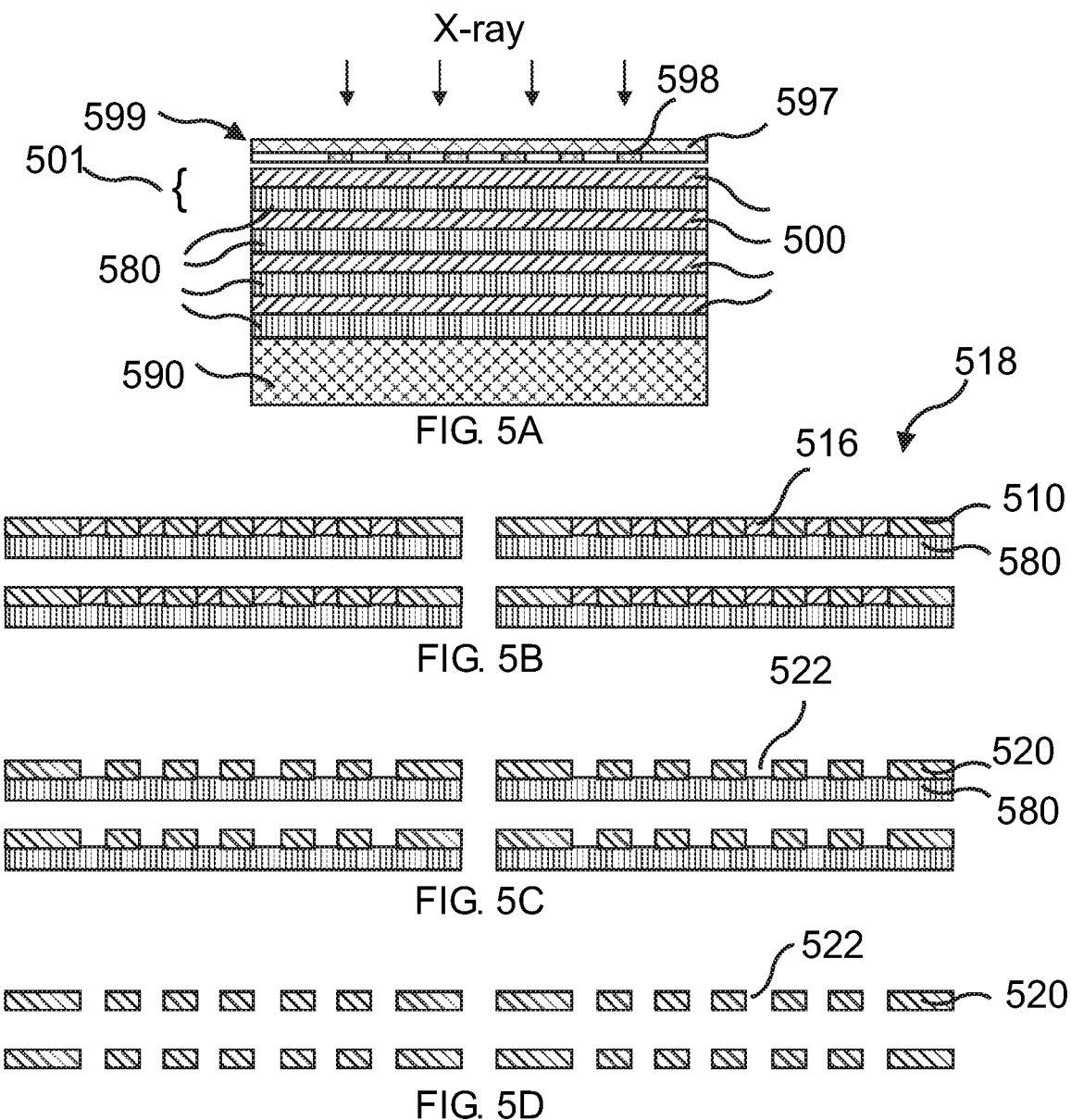

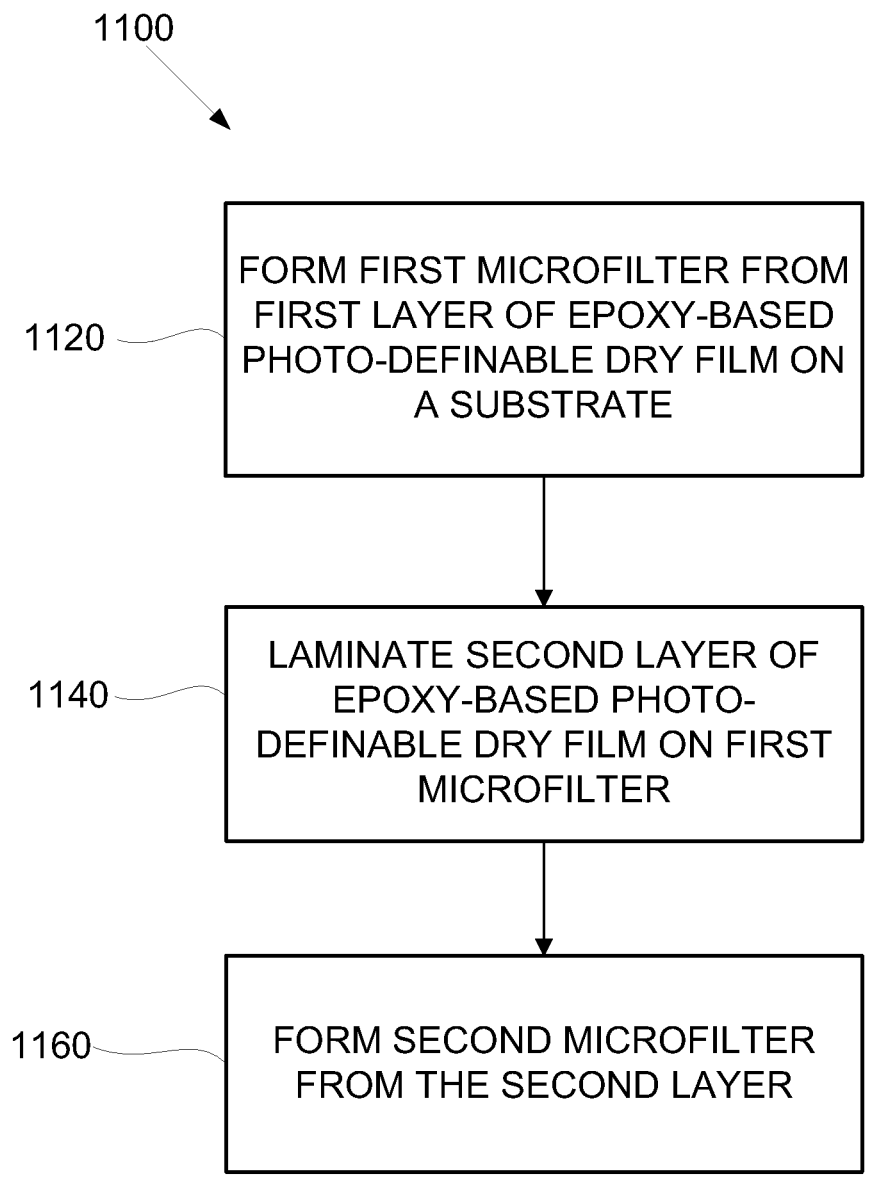

1700

1720 — PASS LIQUID THROUGH A MICROFILTER FORMED FROM EPOXY-BASED PHOTO-DEFINABLE DRY FILM

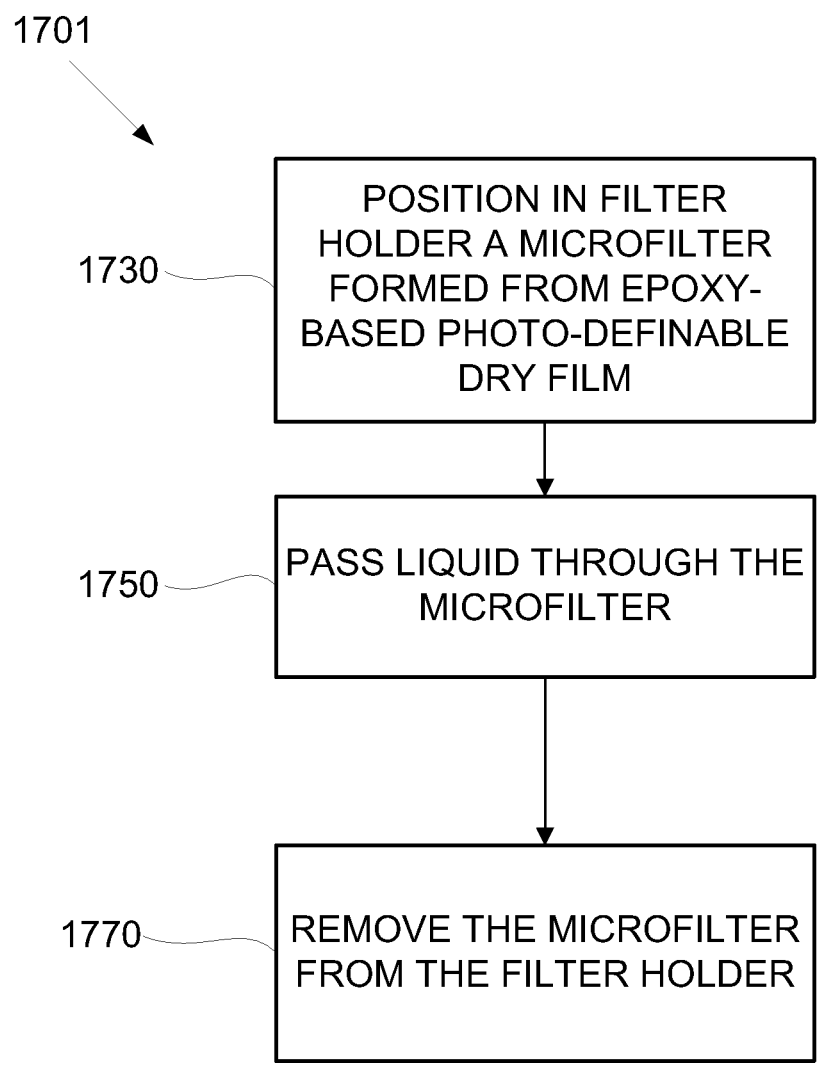

POLYMER MICROFILTERS AND METHODS OF MANUFACTURING THE SAME

CROSS-REFERENCE TO RELATED APPLICATIONS

This application is a national stage application of PCT Application No. PCT/US2011/030966, entitled, "Polymer Microfilters and Methods of Manufacturing the Same," filed on Apr. 1, 2011, which claims priority to U.S. Provisional Patent Application No. 61/330,819, filed May 3, 2010, and U.S. Provisional Patent Application No. 61/377,797, filed Aug. 27, 2010, the contents of which are hereby incorporated by reference herein.

BACKGROUND

Field of the Invention

The present invention relates generally to filtration, and more particularly, to polymer microfilters and methods of manufacturing the same.

Related Art

Some medical conditions may be diagnosed by detecting the presence of certain types of cells in bodily fluid. In particular, cells indicative or characteristic of certain medical conditions may be larger and/or less flexible than other cells found in certain bodily fluids. Accordingly, by collecting such larger and/or less flexible cells from a sample of a bodily fluid, it may be possible to diagnose a medical condition based on the cells collected.

Cells that are larger and/or less flexible than other cells present in a bodily fluid may be collected by filtering the bodily fluid. For example, targeted cells indicative of a condition may be collected by passing a bodily fluid through a filter having openings that are too small for the target cells to pass through, but large enough for other cells to pass through. Once collected, any number of analyses of the target cells may be performed. Such analyses may include, for example, identifying, counting, characterizing, and/or culturing the collected cells.

SUMMARY

In one aspect of the present invention, a microfilter is disclosed. The microfilter comprises a polymer layer formed from epoxy-based photo-definable dry film, and a plurality of apertures each extending through the polymer layer.

In another aspect of the present invention, a multi-layer microfilter is disclosed. The microfilter comprises a first polymer layer formed from epoxy-based photo-definable dry film and having a first aperture extending therethrough, and a second polymer layer formed from epoxy-based photo-definable dry film and having a second aperture extending therethrough, wherein the first and second apertures at least partially define a non-linear passage extending through the first and second layers.

In yet another aspect of the present invention, a method of manufacturing a microfilter is disclosed. The method comprises providing a first layer of epoxy-based photo-definable dry film disposed on a substrate, exposing the first layer to energy through a mask to form a pattern, defined by the mask, in the first layer of dry film, forming, from the exposed first layer of dry film, a polymer layer having a plurality of apertures extending therethrough, the plurality of apertures having a distribution defined by the pattern, and removing the polymer layer from the substrate.

In yet another aspect of the present invention, a method of forming a multi-layer microfilter is disclosed. The method comprises forming a first polymer layer comprising a plurality of first apertures from a first layer of epoxy-based photo-definable dry film disposed on a substrate, laminating a second layer of epoxy-based photo-definable dry film on the first polymer layer, and forming a second polymer layer comprising a plurality of second apertures from the second layer of dry film.

In yet another aspect of the present invention, a method of using a microfilter is disclosed. The method comprises passing a liquid through a plurality of apertures of a microfilter formed from an epoxy-based photo-definable dry film, wherein the microfilter has sufficient strength and flexibility to filter the liquid, and wherein the apertures are sized to allow passage of a first type of bodily fluid cell and to prevent passage of a second type of bodily fluid cell.

BRIEF DESCRIPTION OF THE DRAWINGS

Illustrative embodiments of the present invention are described herein with reference to the accompanying drawings, in which:

FIG. 2A is a flowchart illustrating a process for manufacturing a microfilter in accordance with embodiments of the present invention;

FIG. 2B is a flowchart illustrating a process for forming a microfilter from an exposed dry film in the process illustrated in FIG. 2A, in accordance with embodiments of the present invention;

FIGS. 5A-5D are cross-sectional views illustrating multiple stages in a process for manufacturing a plurality of microfilters from a plurality of layers of epoxy-based photo-definable dry film in accordance with embodiments of the present invention;

FIG. 11 is a flow chart illustrating a process 1300 for manufacturing a multi-layer microfilter in accordance with embodiments of the present invention;

FIG. 17B is a flowchart illustrating a filtration process using a microfilter in accordance with embodiments of the present invention.

DETAILED DESCRIPTION

Figure 1A:
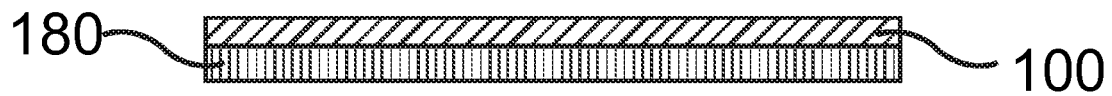
FIGS. 1A-1E are cross-sectional views illustrating multiple stages in a process for manufacturing a microfilter in accordance with embodiments of the present invention.

Aspects of the present invention are generally directed to a microfilter comprising a polymer layer formed from an epoxy-based photo-definable dry film. The microfilter includes a plurality of apertures each extending through the polymer layer. In certain embodiments, the microfilter may be formed by exposing the dry film to energy through a mask and developing the exposed dry film. In some embodiments, the dry film may be exposed to energy in the form of ultraviolet (UV) light. In other embodiments, the dry film may be exposed to energy in the form of X-rays. In certain embodiments, the polymer layer has sufficient strength and flexibility to filter liquid. In some embodiments, the apertures are sized to allow passage of a first type of bodily fluid cell and to prevent passage of a second type of bodily fluid cell.

Specifically, in certain embodiments, the microfilter may be used to perform assays on bodily fluids. In some embodiments, the microfilter may be used to isolate and detect rare cells from a bodily fluid. In certain embodiments, the microfilter may be used to collect circulating tumor cells (CTCs) from blood passed through the microfilter. In some embodiments, cells collected using the microfilter may be used in downstream processes such as cell identification, enumeration, characterization, culturing, etc.

More specifically, in certain embodiments, multiple layers of epoxy-based photo-definable dry film may be exposed to energy simultaneously for scaled production of microfilters. In some embodiments, a stack of epoxy-based photo-definable dry film layers is provided, and all of the dry film layers in the stack are exposed to energy simultaneously. In some embodiments, a dry film structure including epoxy-based photo-definable dry film disposed on a substrate is provided in the form of a roll. In such embodiments, a portion of the structure may be unrolled for exposure of the dry film to energy. In certain embodiments, portions of a plurality of rolls may be exposed to energy simultaneously.

FIGS. 1A-1E are cross-sectional views illustrating multiple stages in a process for manufacturing a microfilter 120 in accordance with embodiments of the present invention. FIG. 2A is a flowchart illustrating a process 200 for manufacturing a microfilter in accordance with embodiments of the present invention. The exemplary process of FIG. 2A will be described below with reference to FIGS. 1A-1E. Other embodiments of the process illustrated in FIG. 2A will be described below with reference to FIGS. 3A-8B.

At block 220 of FIG. 2A, a layer of epoxy-based photo-definable dry film 100 (which may be referred to herein as "dry film 100") disposed on a substrate 180 is provided. In some embodiments, dry film 100 is laminated on substrate 180 at block 220. In certain embodiments, a silicon wafer is coated with a thin layer of metallic material, such as copper, and dry film 100 is laminated on the metallic material at block 220. In other embodiments, a dry film 100 with a substrate 180 already attached may be obtained and provided at block 220. As used herein, an "epoxy-based photo-definable" substance refers to a substance including or formed from a photo-definable epoxy resin, such as a polyfunctional epoxy resin, bisphenol A epoxy resin, epoxidized polyfunctional bisphenol A formaldehyde novolac resin, etc. Examples of photo-definable epoxy resins may be found in U.S. Pat. Nos. 7,449,280, 6,716,568, 6,391,523, and 6,558,868, the contents of which are hereby incorporated by reference herein. Examples of photo-definable epoxy resins may also be found in U.S. Patent Publication Nos. 2010/0068648 and 2010/0068649, the contents of which are hereby incorporated by reference herein. As used herein, an "epoxy-based photo-definable dry film" is a dry film including or formed from an epoxy-based photo-definable substance. Examples of epoxy-based photo-definable dry films that may be used in accordance with embodiments of the present invention may be found in U.S. Pat. Nos. 7,449,280, 6,391,523, and 6,558,868, and U.S. Patent Publication Nos. 2010/0068648 and 2010/0068649. In addition, examples of epoxy-based photo-definable dry films that may be used in accordance with embodiments of the present invention are included in PERMX™ series polymer film from DuPont and SUEX™ sheets from DJ DevCorp, each of which includes a photo-definable layer between two other polymer layers.

In certain embodiments, substrate 180 is a thin copper foil. In some embodiments, smooth substrates are preferable because irregularities in the surface of the substrate to which the dry film is laminated are transferred to a surface of the dry film. In some embodiments, a thin copper film is preferred as a substrate so that the substrate may be removed in a relatively short amount of time. In other embodiments, substrate 180 may be a silicon wafer, a polyimide film such as Kapton, or any other suitable material.

Figure 1B:
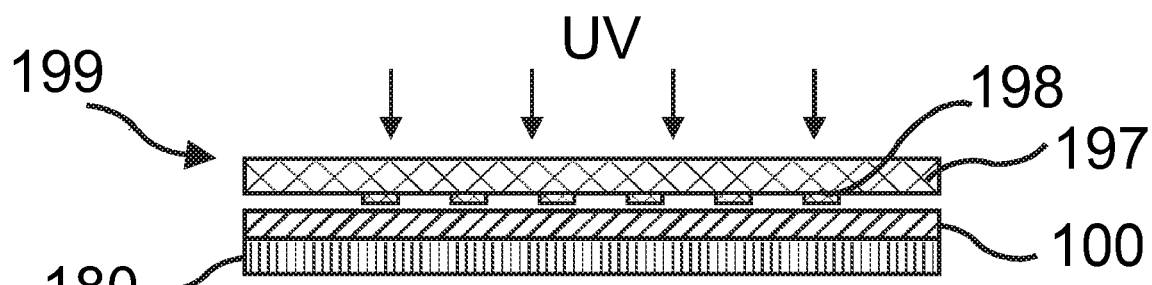
Figure 1C:
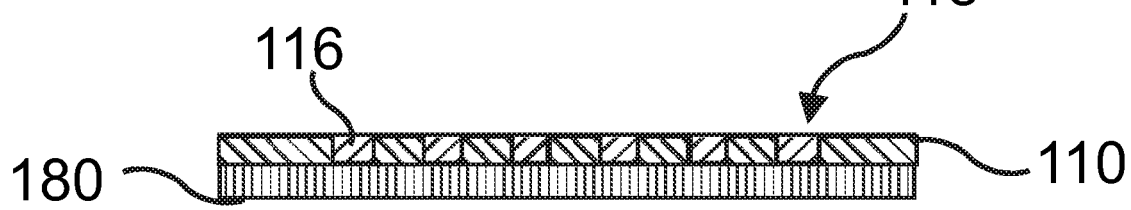
Figure 1D:
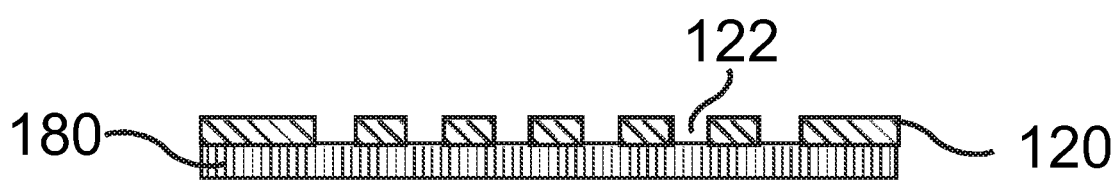

As shown in FIGS. 1B and 1C, dry film 100 is exposed to energy through a mask 199 to form an exposed dry film 110 at block 240. In the embodiment illustrated in FIGS. 1B and 1C, dry film 100 is exposed to energy in the form of ultraviolet (UV) light through an optical mask 199 having a mask portion 197 that is transparent to UV light and a mask pattern 198 formed from a thin film of material that is opaque to UV light. In alternative embodiments, dry film 100 may be exposed to X-rays through an X-ray mask at block 240, instead of being exposed to UV light through optical mask 199.

In the embodiment illustrated in FIGS. 1A-1E, dry film 100 is a negative resist. As used herein, a "negative resist" is a photo-definable substance that becomes polymerized when exposed to certain kinds of energy, such as UV light or X-rays. Examples of negative resist epoxy-based photo-definable dry films that may be used in accordance with embodiments of the present invention include the negative resist dry film included in PERMX™ series polymer film from DuPont, and the negative resist dry film included in SUEX™ sheets from DJ DevCorp, each of which includes a photo-definable layer between two other polymer layers. The PERMX™ 3000 series is manufactured in rolls by Dupont in commercially available thicknesses of 10 μm, 14 μm, 25 μm, and 50 μm, although other thickness can also be obtained.

As shown in FIG. 1C, the portions of exposed dry film 110 that were exposed to UV light through mask 199 become polymerized, leaving portions 116 that are not polymerized. The polymerized and non-polymerized portions of exposed dry film 100 form a pattern 118 that is defined by optical mask 199. More particularly, pattern 118 of exposed dry film 110 is defined by a pattern 198 of optical mask 199, where pattern 198 is formed by material opaque to UV light. In certain embodiments, pattern 198 may be formed by a thin film of material opaque to UV light, such as a thin film of chromium.

In alternative embodiments, a positive epoxy-based photo-definable dry film may be used instead of a negative dry film. In such embodiments, the process for forming a microfilter from the positive dry film is similar to the process for forming a microfilter described in relation to FIGS. 1A-2A, except that a different mask may be used, as described below in relation to FIGS. 4A-4D. As used herein, a "positive resist" is a photo-definable substance in which polymeric bonds are broken when the substance is exposed to certain kinds of energy, such as UV light or X-rays. In certain embodiments, the positive resist may be a resist based on polydimethylglutarimide (such as PMGI, LOR available from MicroChem), an acetate and xylene free resist (such as an S1800® series resist available from Shipley Corp.), or another type of positive resist. For resist layers that are greater than a few microns in thickness, negative resists are generally much more sensitive than positive resists. Most polymer resists belong to the category of positive resist films. Examples of dry film positive resists that may be used include polymethylmethacrylate (PMMA), and a synthetic polymer of methyl methacrylate. Other examples of positive resists are acrylics, polyimide, polyesters, such as polyethylene terephthalate (PET) (MYLAR™), etc. In certain embodiments, a microfilter may be formed from a photo-definable dry film that is not epoxy based, in accordance with embodiments of the present invention. In such embodiments, the dry film may be a positive or a negative resist. In other embodiments, a microfilter may be formed from a photo-definable liquid, rather than a dry film. In such embodiments, the photo-definable liquid may be a positive resist or a negative resist. In certain embodiments, the photo-definable liquid may be liquid polyimide. In such embodiments, the photo-definable liquid polyimide may be positive resist or negative resist.

At block 260, a microfilter 120 having a plurality of apertures 122 extending through the microfilter is formed from exposed dry film 110. In certain embodiments, microfilter 120 includes a polymer layer formed from epoxy-based photo-definable dry film and a plurality of apertures extending through the polymer layer. In each of the embodiments of the present invention described herein, a microfilter includes one or more polymer layers and one or more apertures extending though each of the one or more polymer layers. Also, as used herein, an "aperture" refers to any type of passage, pore, trench, gap, hole, etc., that extends between outer surfaces of a layer or other structure. In the embodiment illustrated in FIGS. 1A-1E, apertures 122 are pores 122.

Figure 1E:
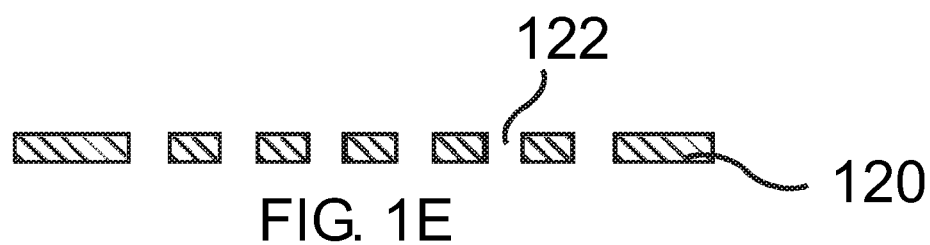

In the embodiment illustrated in FIGS. 1A-1E, exposed dry film 110 is developed to remove non-polymerized portions 116 to form microfilter 120 having pores 122. In certain embodiments, exposed dry film 110 is developed by applying a developer to dry film 110 to dissolve non-polymerized portions 116. In some embodiments, the developer is an aqueous solution that dissolves non-polymerized portions 116 when exposed dry film 110 is submerged in the developer. At block 280, microfilter 120 having pores 122 is removed from substrate 180 to form a free-standing microfilter 120, as shown in FIG. 1E. In some embodiments, a microfilter is a structure of one or more polymer layers including one or more apertures extending between outer surfaces of the structure, wherein the structure has sufficient strength and flexibility to filter a liquid passed through the one or more apertures. In certain embodiments, a microfilter may include apertures having dimensions small enough to prevent one or more types of bodily fluid cells from passing through the apertures when a bodily fluid or liquid containing a bodily fluid is passed through the filter, wherein the dimensions of the apertures are also small enough to prevent one or more other types of bodily fluid cells from passing through the filter. As used herein, "bodily fluid cell" refers to any cell that may be found in a bodily fluid of a patient, such as red or white blood cells, rare cells, such as CTCs and fetal cells, etc. In some embodiments, a microfilter includes apertures sized to allow passage of a significant number of red blood cells and to prevent passage of a significant number of CTCs. In certain embodiments, a microfilter formed from one or more layers of epoxy-based photo-definable dry film may be a polymeric microfilter.

Various embodiments of the process illustrated in FIG. 2A will be described below in relation to FIGS. 2B-8B. As noted above, in certain embodiments, substrate 180 may be copper foil. In such embodiments, copper substrate 180 may be removed from microfilter 120 using nitric acid, ferric chloride or another well known reagent in one variation of block 280. In certain embodiments, the reagent may be used to etch away copper substrate 180 in order to remove it from microfilter 120. In other embodiments, substrate 180 may be another type of metallic foil, such as aluminum, and may be removed at block 280 by well-known methods.

FIG. 2B is a flowchart illustrating a process for forming a microfilter from an exposed dry film at block 260 of FIG. 2A in accordance with embodiments of the present invention. In certain embodiments, the process 260 for forming the microfilter comprises forming, from the exposed dry film, a polymer layer comprising a plurality of apertures. In the embodiment of FIG. 2B, a post bake process is performed on exposed dry film 110 disposed on substrate 180 at block 262. In certain embodiments, the post bake process includes exposing dry film 110 to a relatively high temperature to post bake dry film 110. At block 264, dry film 110 is developed by applying a developer to dry film 110, as described above in relation to FIGS. 1A-1E. At block 266, a hard bake process is performed on the developed dry film 110. In certain embodiments, the hard bake process includes exposing dry film 110 to a relatively high temperature. In some embodiments of the process illustrated in FIG. 2B, the hard bake process of block 266 may be omitted. In such embodiments, microfilter 120 is formed by post baking the exposed dry film 110 at block 262, and developing dry film 110 at block 264. The processes described above in relation to FIG. 2B may be used with any of the embodiments described herein. Additionally, in any of the embodiments of the present invention described here, the process for forming a polymer layer of a microfilter from an epoxy-based photo-definable dry film may include exposing the dry film to energy, performing a post-bake process, developing the exposed dry film, and/or post baking the exposed dry film, as described above.

FIGS. 3A-3E are cross-sectional views illustrating multiple stages in a process for manufacturing microfilter 120 in accordance with embodiments of the present invention. In the embodiment illustrated in FIGS. 3A-3E, the substrate is a polyimide film 181. At block 220, a layer of epoxy-based photo-definable dry film 100 disposed on polyimide film 181 is provided with a separator 182 disposed between a portion of dry film 100 and polyimide film 181. In the embodiment shown in FIG. 3A, a separator 182 is disposed between a portion of dry film 100 and polyimide film 181 along an edge of dry film 100. In certain embodiments, separator 182 may be disposed along one or more edges of dry film 100, or at other locations between dry film 100 and polyimide film 181. Separator 182 may be formed from a polyimide film (such as a KAPTON film) or from any other suitable material that can be laminated to dry film 100 and withstand the temperature of a hard bake process.

Figure 3A:
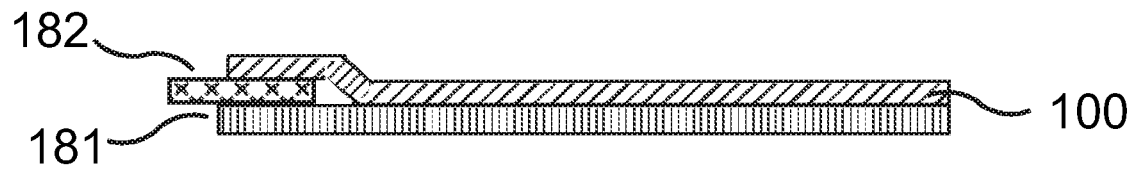
FIGS. 3A-3E are cross-sectional views illustrating multiple stages in a process for manufacturing a microfilter 120 in accordance with embodiments of the present invention.
Figure 3B:
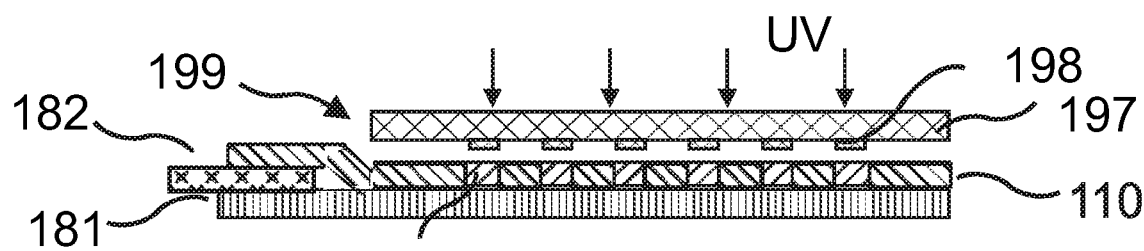
Figure 3C:
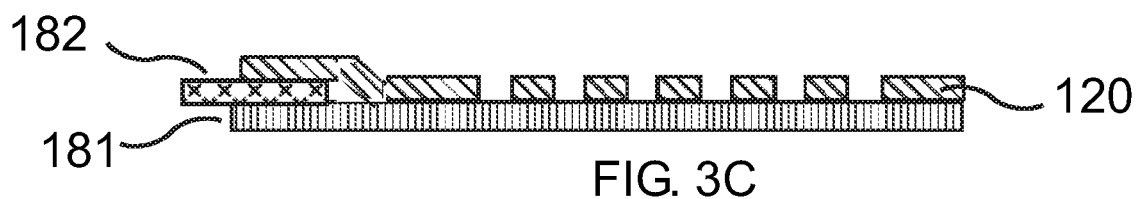
Figure 3D:
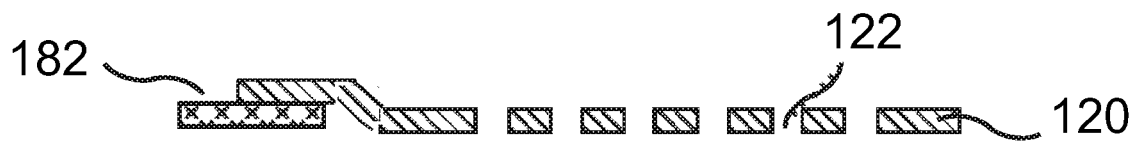
Figure 3E:
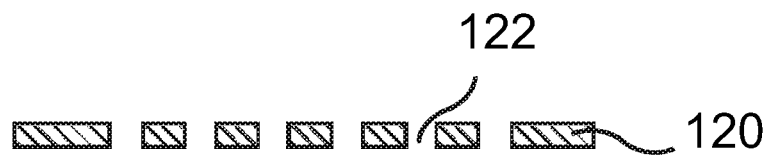

As shown in FIGS. 3B-3C, dry film 100 is exposed to energy, and a microfilter 120 is formed from exposed dry film 110 at blocks 240 and 260, as described above in relation to FIGS. 1B-1D. In certain embodiments, microfilter 120 includes a polymer layer comprising a plurality of apertures therethrough. In the embodiment illustrated in FIGS. 3A-3E, microfilter 120 is removed from polyimide film 181 by grasping an exposed end of separator 182 and using separator 182 to peel microfilter 120 from polyimide film 181. After dry film 100 is removed from polyimide layer 181, as shown in FIG. 3D, separator 182 is removed from dry film 100 to obtain a free-standing microfilter 120, as shown in FIG. 3E. Removing microfilter 120 from layer 181, and removing separator 182 from microfilter 120, are two steps performed in one variation of block 280, in accordance with embodiments of the present invention.

In alternative embodiments of the process illustrated in FIG. 2A, a liquid resist may be used instead of dry film 100. In such embodiments, a substrate is coated with a thin layer of a metallic substance and an epoxy-based liquid photoresist is spin coated onto the metallic substance to provide a layer of an epoxy-based photo-definable substance on a substrate, in one variation of block 210. In certain embodiments, the substrate may be a silicon wafer, the metallic substance may be copper, and the liquid photoresist may be an epoxy-based photo-definable liquid. In some embodiments, the epoxy-based photo-definable liquid is a liquid negative resist, such as SU-8. The layer of the epoxy-based photo-definable substance is exposed to energy, and a microfilter 120 is formed from the exposed layer at blocks 240 and 260, as described above in relation to FIGS. 1B-1D. In one variation of block 280, microfilter 120 is released from the substrate by etching away the metallic substance via conventional processes as described above. In certain embodiments, the liquid resist may be a liquid negative resist, such as SU-8 or KMPR® available from MicroChem Corp.

In other alternative embodiments of the process illustrated in FIG. 2A, a liquid negative resist may be used instead of dry film 100, and a positive resist between the negative resist and the substrate may be used as a release layer. In such embodiments, to provide a layer of an epoxy-based photo-definable substance on a substrate in one variation of block 210, a liquid positive resist is spin coated on a substrate, the positive resist is exposed to energy (such as UV light) at the appropriate dose for the thickness of the coating, and a liquid, epoxy-based negative resist is spin coated on the positive resist. In certain embodiments, the positive resist may be exposed to energy without the use of a mask. The layer of the epoxy-based photo-definable substance is exposed to energy, and a microfilter 120 is formed from the exposed layer at blocks 240 and 260, as described above in relation to FIGS. 1B-1D. In such embodiments, in one variation of block 280, microfilter 120 is released from the substrate by developing the positive resist. In certain embodiments, the same developer may be used to develop both the positive and the negative resists. In other embodiments, one developer may be used to form the pores in microfilter 120, and another developer may be used to release the microfilter from the substrate. In alternative embodiments, a dry film positive resist may be used as the release layer instead of a liquid positive resist. Examples of dry film positive resists that may be used include polymethylmethacrylate (PMMA), and a synthetic polymer of methyl methacrylate.

In other embodiments, a negative epoxy-based photo-definable dry film 100 may be used in combination with a positive resist release layer. Such embodiments are similar to the embodiments described above utilizing a positive resist release layer, except that a layer of the negative dry film 100 may be laminated on the spin coated positive resist at block 210, rather than spin coating a liquid negative resist.

Figure 4A:
FIGS. 4A-4D are cross-sectional views illustrating multiple stages in a process for manufacturing a microfilter in accordance with embodiments of the present invention.
Figure 4B:
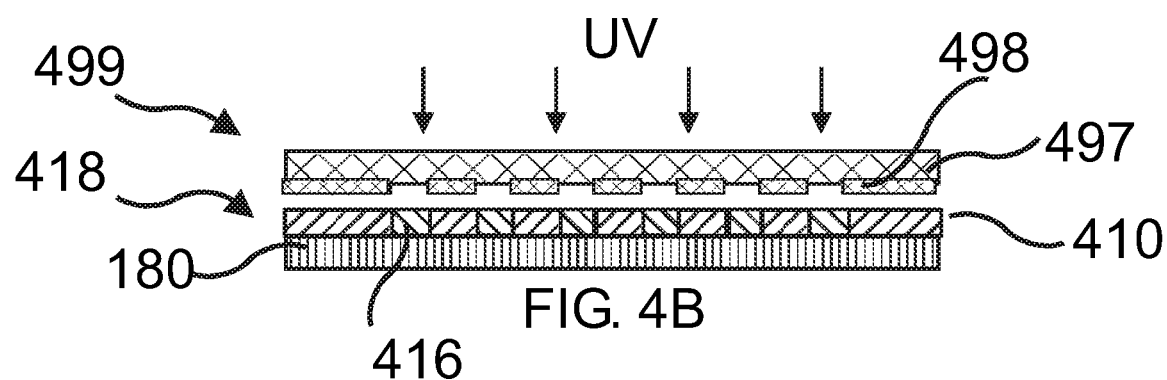
Figure 4C:
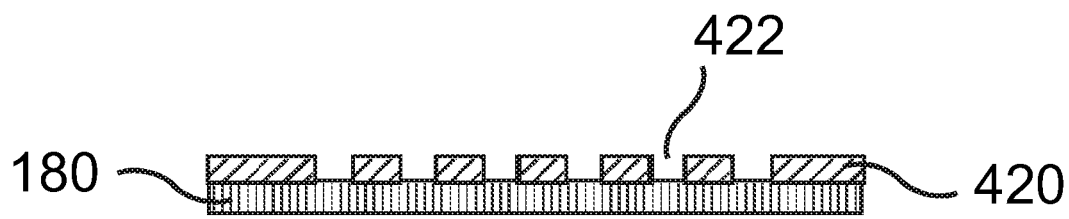

FIGS. 4A-4D are cross-sectional views illustrating multiple stages in a process for manufacturing a microfilter 420 in accordance with embodiments of the present invention. In the embodiment illustrated in FIGS. 4A-4D, a layer of positive, epoxy-based photo-definable dry film 400 (which may be referred to herein as "dry film 400") disposed on substrate 180 is provided at block 220. In certain embodiments, positive dry film 400 is laminated on substrate 180 at block 220. As shown in FIG. 4B, positive dry film 400 is exposed to energy at block 240, as described above in relation to FIGS. 1B and 1C, except that, rather than exposed portions of dry film 400 becoming polymerized, polymeric bonds of dry film 400 are broken at portions 416, which are exposed to energy (e.g., UV light) through mask 499. A pattern 418 of exposed portions 416 and unexposed portions is formed in exposed dry film 410. As shown in FIG. 4B, mask 499 includes a transparent portion 497 and an opaque portion 498. As described above, mask 199 of FIG. 1B is used with a negative resist and is configured to cover portions of dry film 100 where pores will be formed in dry film 100. In the embodiment illustrated in FIGS. 4A-4D, opaque portions 498 of mask 499 are configured to cover all portions of positive dry film 400 except the locations where apertures will be formed, allowing UV light to pass through mask 499 to positive dry film 400 at locations where apertures are to be formed in positive dry film 400.

Figure 4D:
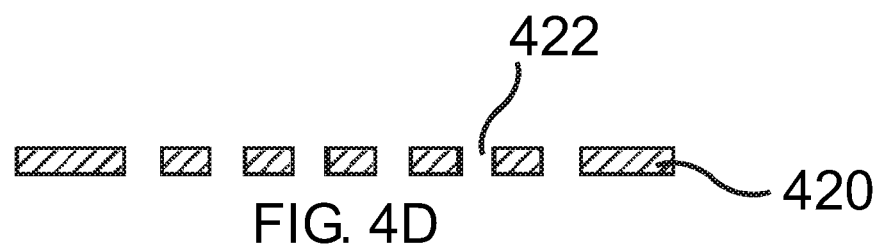

In the embodiment illustrated in FIGS. 4A-4D, a microfilter 420 is formed from exposed dry film 410 in one variation of block 260, by developing dry film 410 using a developer that dissolves the portions 416 of dry film 400 where the polymeric bonds were broken. At block 280, microfilter 420 having apertures 422 is removed from substrate 180 to form a free-standing polymeric microfilter 420, as shown in FIG. 4D. In some embodiments, microfilter 420 includes a polymer layer formed from epoxy-based photo-definable dry film and includes a plurality of apertures extending through the polymer layer. In certain embodiments, the apertures 422 are pores 422. In some embodiments, at block 280, microfilter 420 may be released from the substrate by developing the positive resist, as described above.

FIGS. 5A-5D are cross-sectional views illustrating multiple stages in a process for manufacturing a plurality of microfilters from a plurality of layers of epoxy-based photo-definable dry film in accordance with embodiments of the present invention. In certain embodiments of the process illustrated in FIG. 2A, a plurality of dry film structures 501, each including a layer of epoxy-based photo-definable dry film 500 (which may be referred to herein as "dry film 500") disposed on a substrate 580, are provided at block 220. In the embodiment illustrated in FIGS. 5A-5D, dry films 500 disposed on substrates 580 are provided at block 220 by stacking structures 501 on a support 590, as illustrated in FIG. 5A.

In certain embodiments, as illustrated in FIG. 5A, dry films 500 in the stack of structures 501 are simultaneously exposed to energy in the form of X-rays through an X-ray mask 599 at block 240 of FIG. 2A. In some embodiments, the penetration of X-rays is much deeper than UV light. Unlike UV light, X-rays do not diverge within a material having a thickness of less than 5 mm, even for features significantly smaller than one micron. In some embodiments, X-ray lithography may be typically performed on a beamline of a synchrotron. In addition, X-ray lithography can be used for both negative and positive resists. In the embodiment illustrated in FIGS. 5A-5D, dry films 500 are each negative resists. In other embodiments, dry films 500 may be positive resists. In such embodiments, a mask configured to form apertures in a positive resist, as described above in relation to mask 499 of FIG. 4B, may be used. Additionally, in embodiments in which dry films 500 are positive resists, dry films 500 may be may be attached to support 290 and stacked directly on one another, without each being disposed on a respective substrate.

As shown in FIG. 5B, the portions of each dry film 500 exposed to X-rays through mask 599 become polymerized, leaving portions 516 of dry film 500 that are not polymerized. The polymerized and non-polymerized portions of each dry film 500 form a pattern 518 that is defined by pattern 598 of optical mask 599. In some embodiments, mask 599 includes an X-ray transparent portion 597, and a pattern 598 configured to substantially block X-rays. In certain embodiments, pattern 598 is formed from gold. In addition, in some embodiments, X-ray transparent portion 597 may be a thin graphite sheet or a silicon wafer. In the embodiment illustrated in FIGS. 5A-5D, each of substrates 580 transmits most of the X-ray energy applied to it. In certain embodiments, substrates 580 are formed from a metallic foil. In such embodiments, when the foil is sufficiently thin, each substrate 580 will transmit most of the X-ray energy applied to it. In some embodiments, the number of structures 501 that may be stacked and then exposed simultaneously is based on the reduction in the dose of the X-rays caused by the X-rays passing through the metallic foil.

In certain embodiments, in one variation of block 260, the plurality of exposed dry films 510 are developed to form a plurality of microfilters 520 each having apertures 522 in a manner similar to that described above in relation to FIGS. 1A-1E. In certain embodiments, apertures 522 are pores 522. In some embodiments, the process illustrated in FIGS. 5B and 5C may be performed in one variation of block 260. In such embodiments, structures 501 are separated from one another, as shown in FIG. 5B, and a post bake procedure is performed on exposed dry films 510 disposed on respective substrates 580 in one variation of block 262. In certain embodiments, each of exposed dry films 510 is developed, as described above, in one variation of block 264 to form pores 522 in each of dry films 500, as shown in FIG. 5C. In some embodiments, a hard bake procedure is performed on dry films 510 disposed on respective substrates 580, in one variation of block 266, to form microfilters 520 having pores 522. In other embodiments, the hard bake procedure may be omitted. In certain embodiments, in one variation of block 280, substrates 580 are chemically removed from microfilters 520, as described above, to obtain free-standing microfilters 520 having pores 522, as shown in FIG. 5D. In certain embodiments, each of microfilters 520 is a polymer layer including apertures 522.

As described above, in certain embodiments, each of substrates 580 may be formed from a metallic foil. In alternative embodiments, substrate 580 may be a polymer based substrate that transmits most of the X-rays applied to it, and which has a melting point higher than a post bake temperature for dry film 500. For example, in certain embodiments, substrate 580 may be formed from a positive resist. In such embodiments, substrate 580 may be exposed to energy, such as UV light or X-rays, sufficient to break polymeric bonds in the positive resist such that substrate 580 may be removed chemically by a developer solution at block 280 of FIG. 2A. In other embodiments, substrate 580 may be a polyimide film and may be removed at block 280 by peeling the polyimide substrate 580 from microfilter 520.

In alternative embodiments, layers of epoxy-based photo-definable dry film 500 (which may be referred to as "dry films 500") may be stacked and simultaneously exposed without each of the layers being disposed on a respective substrate. In such embodiments, in one variation of block 220, dry films 500 are stacked on a support 590 without substrates disposed between adjacent dry films 500. The stacked dry films 500 are exposed in one variation of block 240. In some embodiments, the process illustrated in FIG. 2B may be performed at block 260. In such embodiments, the exposed dry films 510 may be separated and placed on separate substrates on which exposed dry films 510 undergo a post bake process in one variation of block 262. In such embodiments, the substrates used are able to withstand the post bake temperature and can be dissolved by water or one or more chemicals. While attached to respective substrates, exposed dry films 510 are developed at block 264 and may undergo a hard bake procedure at block 266. At block 280, the substrates 580 are removed from the microfilters 520 formed from exposed dry films 510.

Figure 6A:
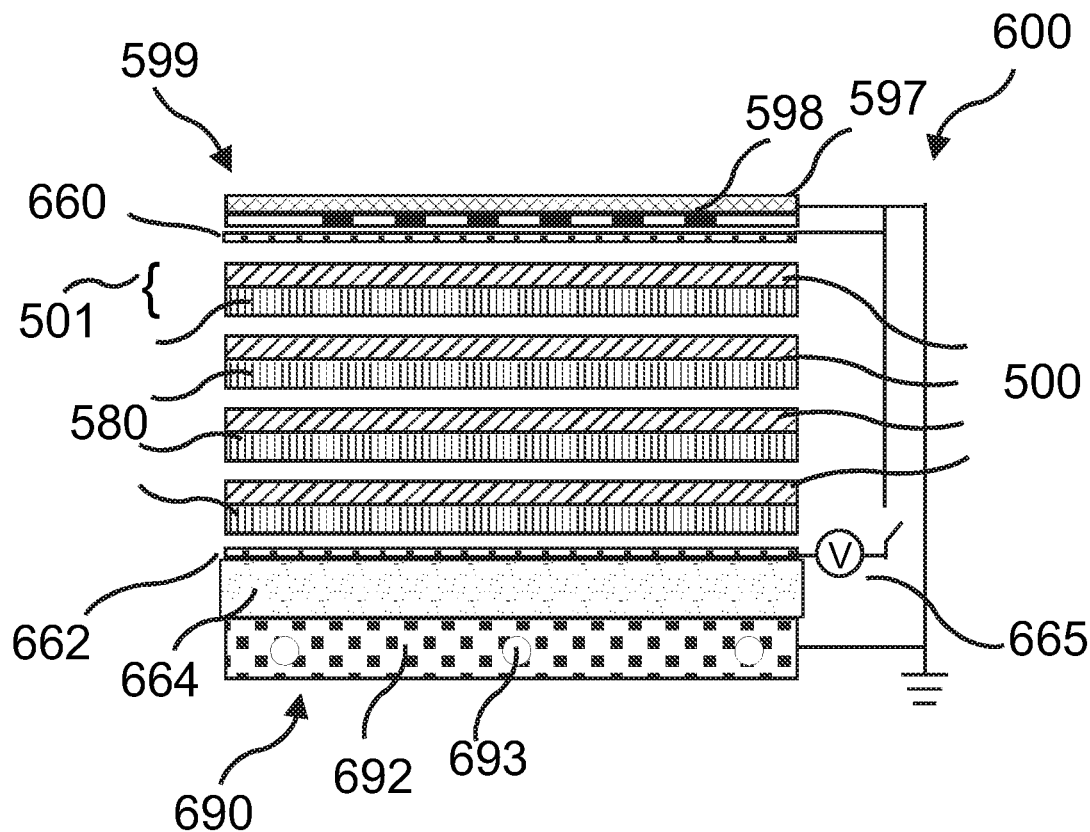
FIGS. 6A and 6B are cross-sectional views illustrating multiple stages in a process for attaching dry film structures to a support using an electrostatic chuck apparatus in a process for forming microfilters in accordance with embodiments of the present invention.
Figure 6B:
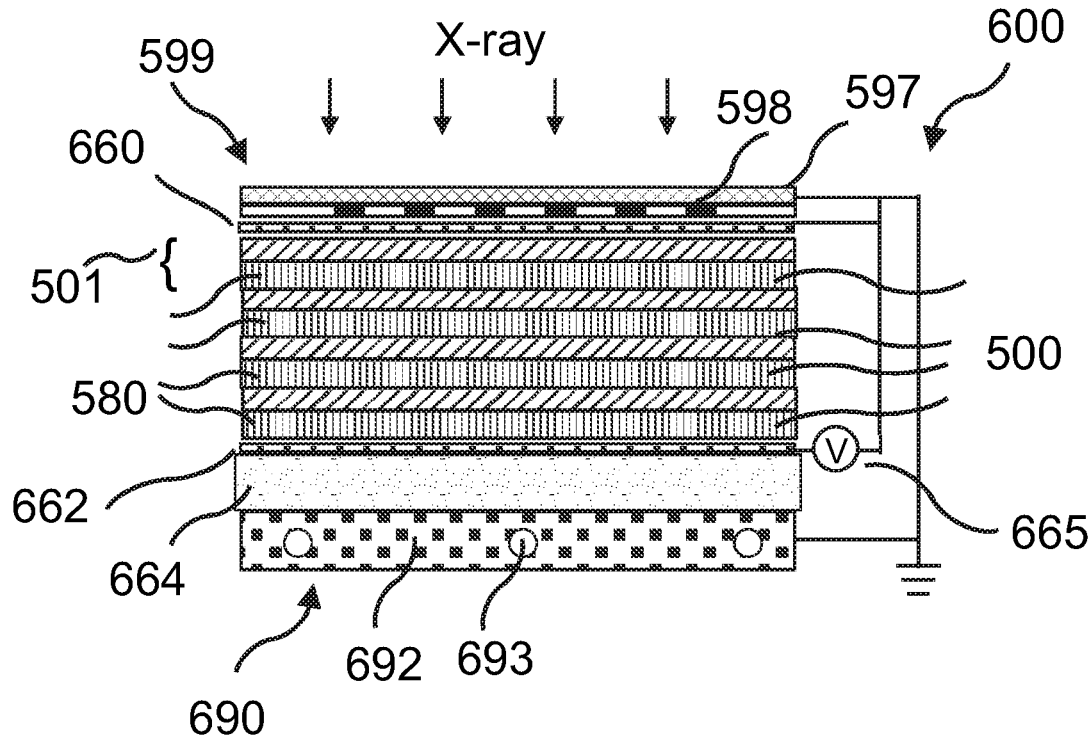

In certain embodiments, structures 501 may be attached to support 590 using adhesive, a clamp, or any other suitable mechanism or method. In some embodiments, structures 501 are held to a support by an electrostatic chuck. FIGS. 6A and 6B are cross-sectional views illustrating multiple stages in a process for attaching dry film structures 501 to a support using an electrostatic chuck apparatus 600 in a process for forming microfilters in accordance with embodiments of the present invention. In the embodiment illustrated in FIGS. 6A and 6B, a plurality of dry film structures 501, each including a layer of epoxy-based photo-definable dry film 500 disposed on a substrate 580, are provided stacked on a support 690, as shown in FIG. 6A. As shown in FIG. 6A, support 690 includes a water cooling frame 692 with a duct 693, an insulator 664 disposed on frame 692, and a conductive layer 662 disposed on insulator 664. Additionally, a transparent conductive layer 660 is placed on the stack of structures 501 such that the stack of structures 501 is disposed between conductive layers 660 and 662, as shown in FIG. 6A. Also as shown in FIG. 6A, a circuit connecting the conductive layers is open so that a voltage 665 of zero is applied to the conductive layers.

As shown in FIG. 6B, closing the circuit between the conductive layers and applying a non-zero voltage 665 between conductive layers 660 and 662 causes apparatus 600 to press together structures 501 between conductive layers 660 and 662. With structures 501 pressed together by apparatus 600, X-rays may be applied to dry films 500 through X-ray mask 599, as described above in relation to FIGS. 5A-5D. In certain embodiments, stacking structures 501 on apparatus 600 and pressing together structures 501 using apparatus 600, as described above in relation to FIGS. 6A and 6B, may be performed in one variation of block 220 of FIG. 2A. While the use of an electrostatic chuck apparatus has been described above in relation to forming microfilters from dry films each disposed on a respective substrate, in alternative embodiments, an electrostatic chuck may similarly be used to press together a stack of free standing polymeric films, such as free standing dry films, that are not each attached to a respective substrate. Such free standing dry films may be stacked and pressed together during a process for forming a plurality of microfilters from the plurality of dry films.

Figure 7A:
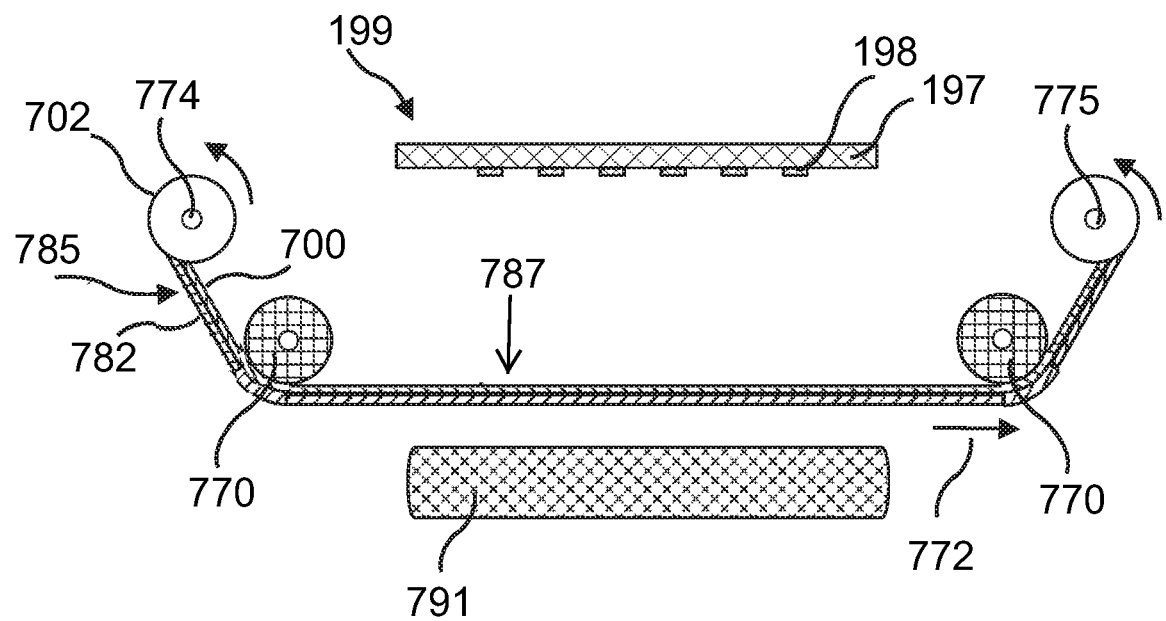
FIGS. 7A and 7B are cross-sectional views illustrating multiple stages in a process for manufacturing microfilters from a roll of a dry film structure in accordance with embodiments of the present invention.
Figure 7B:
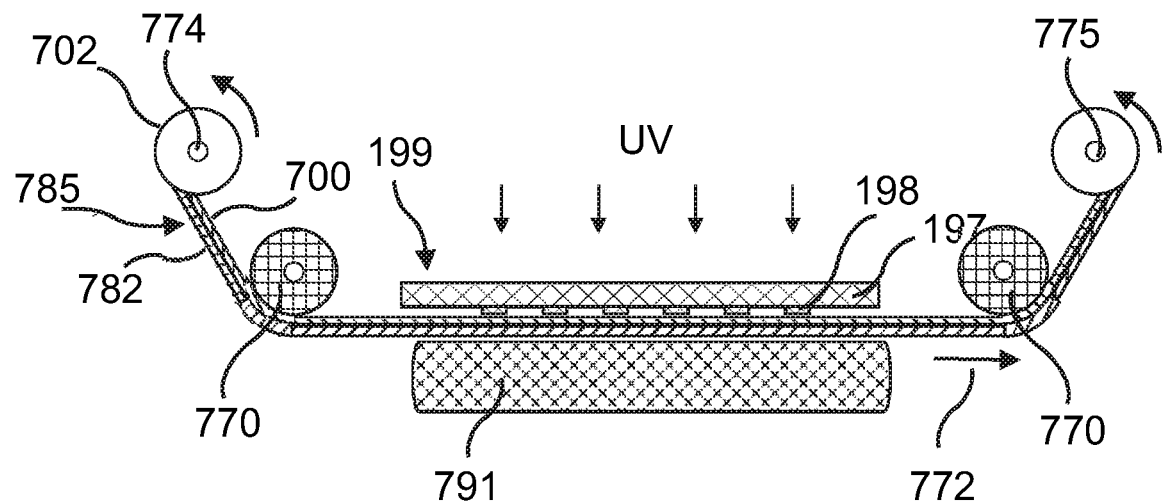

FIGS. 7A and 7B are cross-sectional views illustrating multiple stages in a process for manufacturing microfilters from a roll of a dry film structure in accordance with embodiments of the present invention. In the embodiment illustrated in FIGS. 7A and 7B, a dry film structure 785 is provided in the form of a roll 702 of the dry film structure 785. Dry film structure 785 includes a layer of epoxy-based photo-definable dry film 700 (which may be referred to herein as "dry film 700") disposed on a removable substrate 782. In some embodiments, substrate 782 may be a chemically dissolvable metallic foil. In certain embodiments, the metallic foil may include aluminum or copper, which may be etched away as described above. In the embodiment illustrated in FIGS. 7A and 7B, a portion of roll 702 is disposed on a roller 774 and another portion is disposed on a roller 775. A working portion 787 of dry film structure 785 extends between rollers 774 and 775 and is held substantially flat by rollers 770 for exposure to energy through mask 199.

In certain embodiments of the process illustrated in FIG. 2A, a layer of epoxy-based photo-definable dry film 700 disposed on a substrate 782 is provided, in one variation of block 220, by unrolling a portion of dry film structure 785 from roll 702 and advancing the portion of structure 785 in the direction of arrow 772 to provide working portion 787 of structure 785 between support 791 and mask 199. In some embodiments, the working portion 787 provided at block 220 includes a portion of dry film 700 that has not been patterned by exposure to energy through a mask. In certain embodiments, support 791 and mask 199 are moved away from structure 785 when structure 785 is advanced.

In the embodiment illustrated in FIGS. 7A and 7B, mask 199 and support 791 are moved adjacent to structure 785, and dry film 700 is exposed to energy through mask 199, as shown in FIG. 7B, in one variation of block 240 of FIG. 2A. In the embodiment shown in FIGS. 7A and 7B, mask 199 is an optical mask and the energy is UV light, although a different type of energy may be used along with a different mask, as described above. In the embodiment illustrated in FIGS. 7A and 7B, dry film 700 is a negative resist. In other embodiments, dry film 700 may be a positive resist. In such embodiments, a mask configured to form pores in a positive resist, as described above in relation to mask 499 of FIG. 4B, may be used. Exposing dry film 700 to energy through the mask forms a pattern in dry film 700, as described above in relation to other embodiments. In certain embodiments, support 791 presses against structure 785, as shown in FIG. 7B, to stretch dry film 700 for the exposure process to thereby provide additional tension and stability to dry film 700 during the exposure process. In some embodiments, after exposing dry film 700, structure 785 may be advanced again as described above, to provide a new working portion 787 that has not yet been exposed at block 220, and the new working portion 787 may be exposed at block 240, as described above. In certain embodiments, this process of advancing structure 785 and exposing dry film 700 may be continuously repeated. In some embodiments, the process may be repeated until most or all portions of dry film 700 have undergone an exposure process.

In some embodiments, a microfilter having apertures is formed from an exposed portion of dry film 700 by developing the exposed portion, as described above in relation to other embodiments, in one variation of block 260. In such embodiments, the exposed portion of dry film 700 may be developed before it is rolled onto roller 775, or may be developed after all desired portions of dry film 700 have been exposed. In some embodiments, the process illustrated in FIG. 2B may be performed at block 260. In such embodiments, the exposed portion of dry film 700 may be advanced through an oven for a post bake procedure at block 262, the exposed portion of dry film 700 may be developed at block 264, and then undergo a hard bake procedure at block 266. In other embodiments, the procedures at blocks 262, 264 and 266 may be performed after all desired portions of dry film 700 have been exposed. In certain embodiments, the hard bake procedure may be omitted.

In some embodiments, after developing the exposed dry film 700, substrate 782 is removed at block 280, as described above in relation to other embodiments. In certain embodiments, after removing substrate 782, individual microfilters are diced from the roll of dry film from which the microfilters were formed. In certain embodiments, forming microfilters from a dry film provided as a roll may simplify the manufacture of microfilters in accordance with embodiments of the present invention, and may allow automation of the manufacturing process.

Figure 8A:
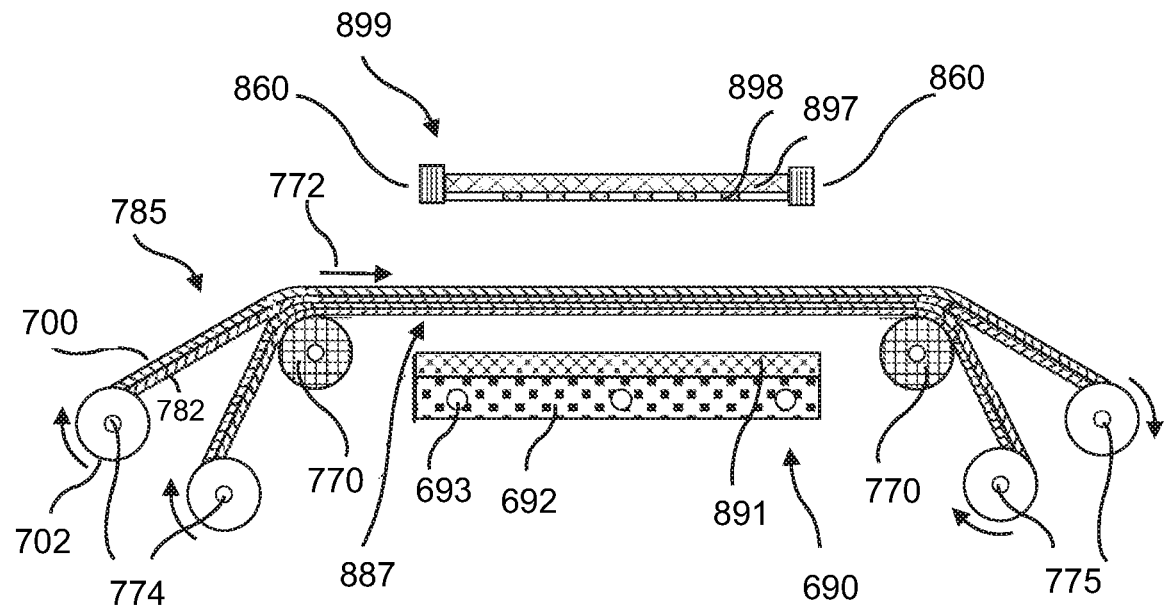
FIGS. 8A and 8B are cross-sectional views illustrating multiple stages in a process for manufacturing microfilters from a plurality of rolls of dry film structures in accordance with embodiments of the present invention.
Figure 8B:
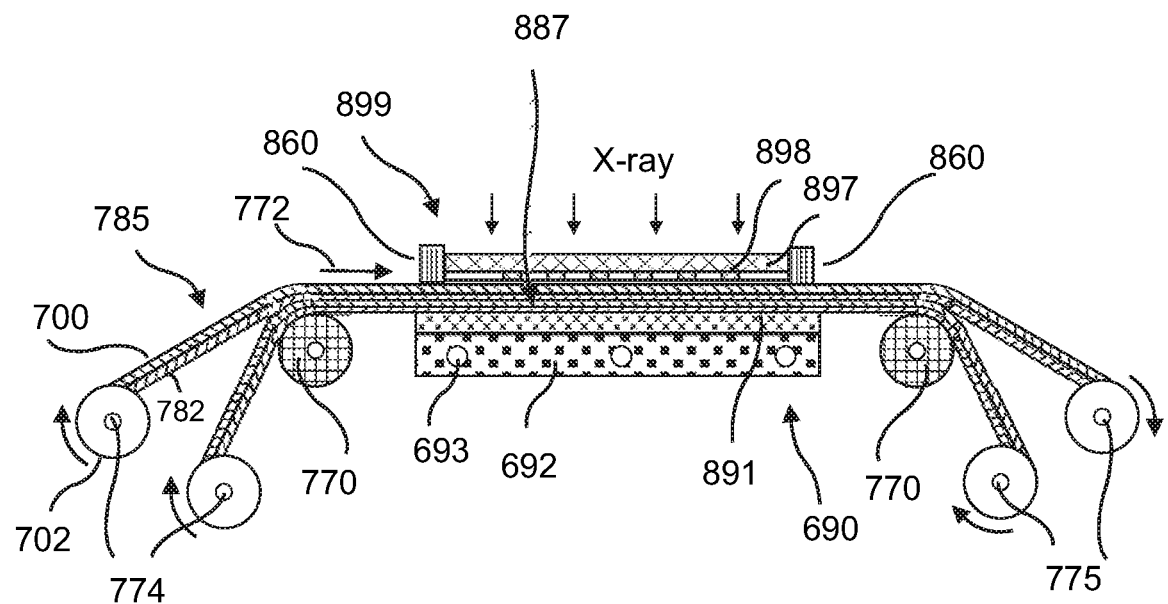

FIGS. 8A and 8B are cross-sectional views illustrating multiple stages in a process for manufacturing microfilters from a plurality of rolls of dry film structures in accordance with embodiments of the present invention. The embodiment illustrated in FIGS. 8A and 8B is similar to the embodiment illustrated in FIGS. 7A and 7B, except that layers of epoxy-based photo-definable dry film 700 of multiple rolls 702 are exposed to energy simultaneously. In such embodiments, a plurality of layers of epoxy-based photo-definable dry film 700 each disposed on a respective substrate 782 are provided, in one variation of block 220, by advancing the structure 785 of each roll 702 in the direction of arrow 772 to provide a stack 887 of structures 785 between support 891 and mask 899. In the embodiment illustrated in FIGS. 8A and 8B, mask 899 and support 891 are moved adjacent to the stack 887, and the portions of dry films 700 in stack 887 disposed between mask 899 and support 891 are exposed to energy simultaneously through mask 899, as shown in FIG. 8B, in one variation of block 240 of FIG. 2A. In the embodiment illustrated in FIGS. 8A and 8B, dry films 700 are each negative resists. In other embodiments, dry films 700 may be positive resists. In such embodiments, a mask configured to form apertures in a positive resist, as described above in relation to mask 499 of FIG. 4B, may be used. Further processes for forming microfilters from dry films 700 are similar to the processes described above in relation to the embodiment illustrated in FIGS. 7A and 7B.

In the embodiment illustrated in FIGS. 8A and 8B, support 891 is disposed on a water cooling frame 692 including a duct 693. In addition, as shown in FIG. 8B, working portions 887 of structure 785 may be securely held in place between support 891 and mask 899 by a clamp 860. In alternative embodiments, stack 887 may be held secure using an electrostatic chuck, as described above in relation to other embodiments. In some embodiments, the number of dry films 700 exposed simultaneously may be determined based on the precision yielded when exposing a stack of a particular number of films. In certain embodiments, forming microfilters from a plurality of dry films provided as a plurality of rolls, as described above, may simplify the manufacture of microfilters and/or facilitate high volume production of microfilters.

In embodiments in which non-epoxy-based dry films are used, the dry films may be provided in roll form without a substrate. In such embodiments, each roll 702 includes only the dry film and not any substrate. In embodiments in which epoxy-based dry films are used, each roll 702 may include an additional cover layer on dry film 700. In such embodiments, substrate 782 is disposed on a first side of dry film 700 and the cover layer on the opposite side of dry film 700. In certain embodiments, lithography-based microfabrication in accordance with embodiments of the present invention may enable efficient mass production of highly uniform precision microfilters. In certain embodiments, fabricating microfilters in accordance with embodiments of the present invention may yield increased porosity and pore uniformity in the microfilters produced.

FIGS. 9A-9D are partial top views illustrating various microfilters aperture distributions in accordance with embodiments of the present invention. In certain embodiments, microfilters having different aperture sizes, shapes and distributions may be provided. In some embodiments, certain combinations of aperture size, shape and distribution may be more advantageous than others for a particular application of a microfilter. For example, for the microfiltration of rare cells, such as circulating tumor cells and fetal cells in blood, a microfilter having round pores each having a diameter of 7-8 microns may be preferable in certain embodiments. In some applications, a microfilter having round pores each with a diameter of 7-8 microns can trap the rare cells while retaining a very small percentage of blood cells.

Figure 9A:
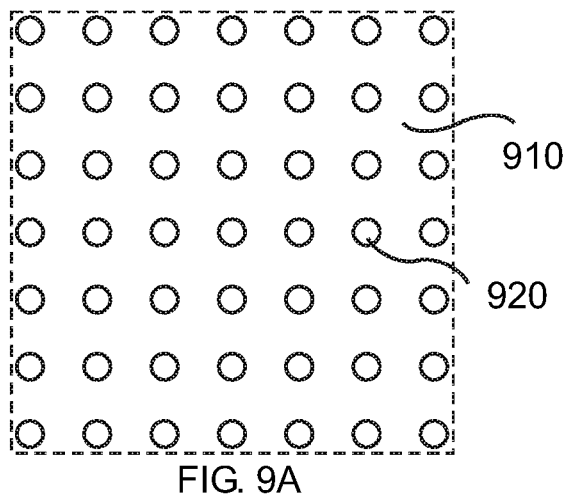
FIGS. 9A-9D are partial top views illustrating various microfilters aperture distributions in accordance with embodiments of the present invention.
Figure 9B:
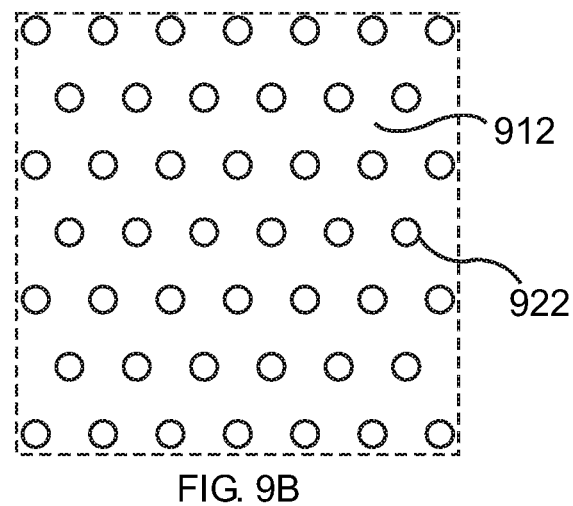
Figure 9C:
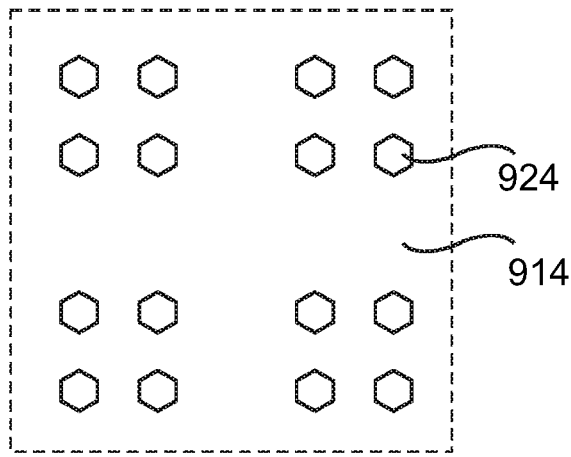
Figure 9D:
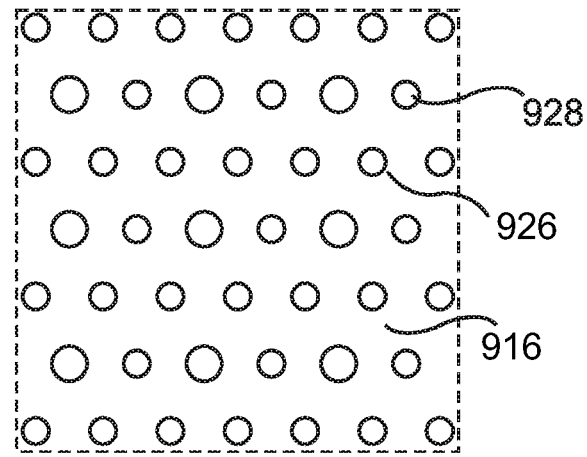

In the embodiments illustrated in FIGS. 9A and 9B, microfilters 910 and 912 each have a uniform distribution of pores 920 and 922, respectively. Additionally, pores 920 are uniform in size, as are pores 922. In the embodiment illustrated in FIG. 9C, microfilter 914 includes uniform pores 924, distributed over microfilter 914 in several groupings of pores 924. In the embodiment illustrated in FIG. 9D, microfilter 916 a plurality of pores 926 of a first size, and a plurality of pores 928 of a second size. In other embodiments, any or pores 920, 922, 924, 926 and 928 may be any other type of aperture. Any of microfilters 910, 912, 914 and 916 may be manufactured using any of the microfilter manufacturing processes described above in accordance with embodiments of the present invention. Additionally, any of the microfilter manufacturing processes described above in accordance with embodiments of the present invention may be used to form apertures of a plurality of different cross-sectional shapes. For example, in certain embodiments, apertures may be formed which have the cross-sectional shape of a circle, triangle, square, rectangle, ellipse, oval, trapezoid, parallelogram, etc.

Figure 10A:
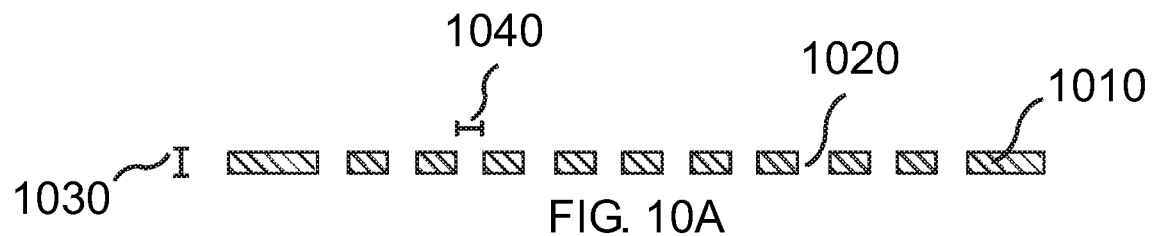
FIGS. 10A-10D are cross-sectional views illustrating microfilters having various thicknesses and various aperture shapes, sizes and distributions in accordance with embodiments of the present invention.
Figure 10B:
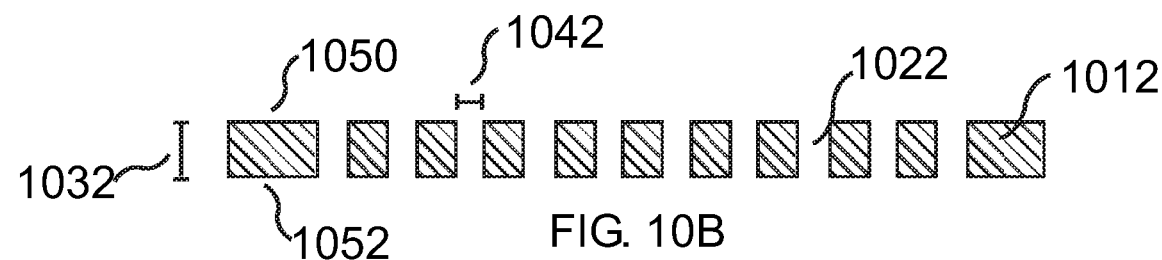
Figure 10C:
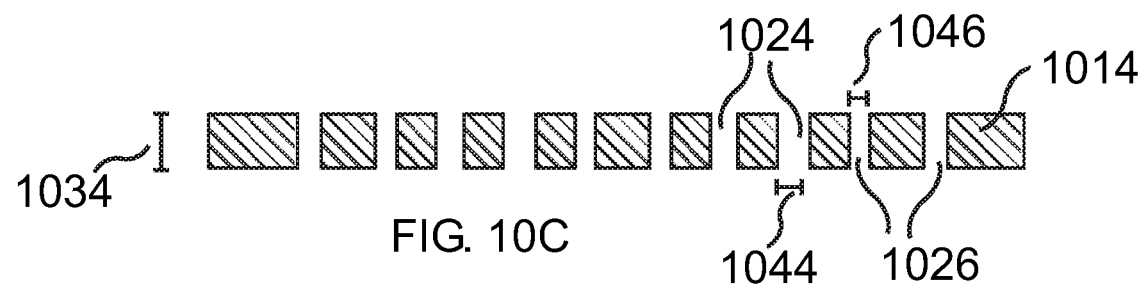

Microfilters having various thicknesses and various aperture shapes, sizes and distributions may be manufactured in accordance with embodiments of the present invention described herein. FIGS. 10A-10D are cross-sectional views illustrating microfilters having various thicknesses and various aperture shapes, sizes and distributions in accordance with embodiments of the present invention. FIGS. 10A and 10B show microfilters 1010 and 1012, each formed via one of the processes described above in accordance with embodiments of the present invention. Microfilter 1010 includes a plurality of pores 1020, each having a width 1040. Microfilter has a thickness 1030 substantially perpendicular to the width 1040 of pores 1020. In the embodiment illustrated in FIG. 10A, thickness 1030 is not significantly larger than width 1040. In certain embodiments, it is preferable that the thickness of the microfilter is on the same order as the width of one or more pores of the microfilter in order to reduce the pressure required to pass a sample through the pores. In some applications, if the thickness of a microfilter is significantly greater than the width of some or all of the pores, a much larger amount of pressure may be applied to the microfilter to pass a sample through a microfilter than if the microfilter has a thickness on the same order as some or all of the pores. Passing the sample through the filter with a relatively large amount of pressure may distort the shape of one or more pores, or risk breaking the microfilter.

For example, for the microfiltration of rare cells, such as CTCs and fetal cells in blood, a microfilter having a thickness of 8-14 microns may be preferable in certain embodiments. In certain embodiments, a microfilter for such an application may have pores each having a diameter of 7-8 microns and a thickness of 8-14 microns. In other embodiments, a microfilter for such applications may include a rectangular aperture having a width of between 5-7 microns and a length greater than 7 microns, wherein the length and width of the aperture are both substantially perpendicular to the thickness of the microfilter. In certain embodiments, the rectangular aperture may be an elongate trench. In certain embodiments, it may be preferred that the width of the apertures in the microfilter are near in size to the thickness of the microfilter. In some embodiments, the thickness of the microfilter is less than ten times the width of some or all the pores. In other embodiments, the thickness of the microfilter is within 10 microns of the width of some or all of the pores. Microfilters formed in accordance with embodiments of the present invention may be used in applications other than capturing circulating tumor cells from blood. In some embodiments, the desired aperture geometry, aperture dimensions, aperture distribution, microfilter materials, microfilter thickness, microfilter size, etc., may vary for different applications. In some embodiments, desired aperture geometry, dimensions, and distribution may be provided by using an appropriate mask, such as an optical or X-ray mask. In certain embodiments, a consideration for microfilters is strength of the material from which the microfilter is made to prevent breakage of the filter material or distortion of the aperture shape.

Figure 10D:
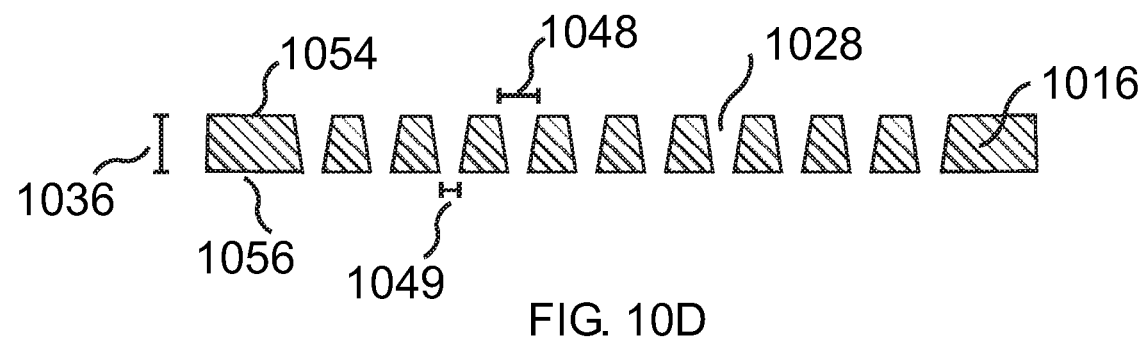

As shown in FIG. 10B, microfilter 1012 has a plurality of pores 1022 each having a width 1042. Microfilter 1012 also has a thickness 1032 that is substantially perpendicular to the width 1042 of pores 1022. The thickness 1032 of microfilter 1012 is greater than the thickness of microfilter 1010. In the embodiment illustrated in FIG. 10B, pores 1022 are uniform in size and are each substantially perpendicular to a first surface 1050 and a second surface 1052 of microfilter 1012. In the embodiment illustrated in FIG. 10C, microfilter 1014 has pores 1024 with a first width 1044 and pores 1026 with a second width 1046 that is smaller than the first width 1044. Microfilter 1014 also has a thickness 1034. In the embodiment illustrated in FIG. 10D, microfilter 1016 has pores 1028 with non-uniform cross-sectional shapes. Each pore 1028 has a first opening in a first surface 1054 of microfilter 1016 and a second opening in a second surface 1056 of microfilter 1016. As shown in FIG. 10D, the width 1048 of pore 1028 at the first surface 1054 is greater than the width 1049 of pore 1028 at the second surface 1056. Microfilter 1016 also has a thickness 1036.

Figure 12A:
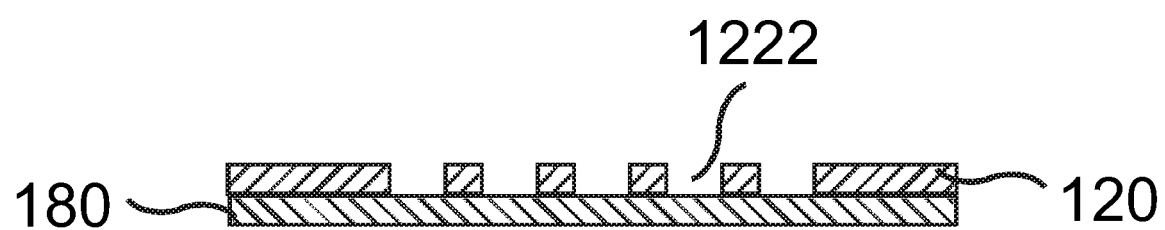
FIGS. 12A-12K are cross-sectional views illustrating multiple stages in a process for manufacturing a multi-layer microfilter in accordance with embodiments of the present invention.
Figure 12B:
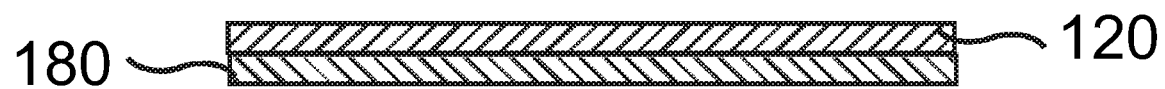
Figure 13A:
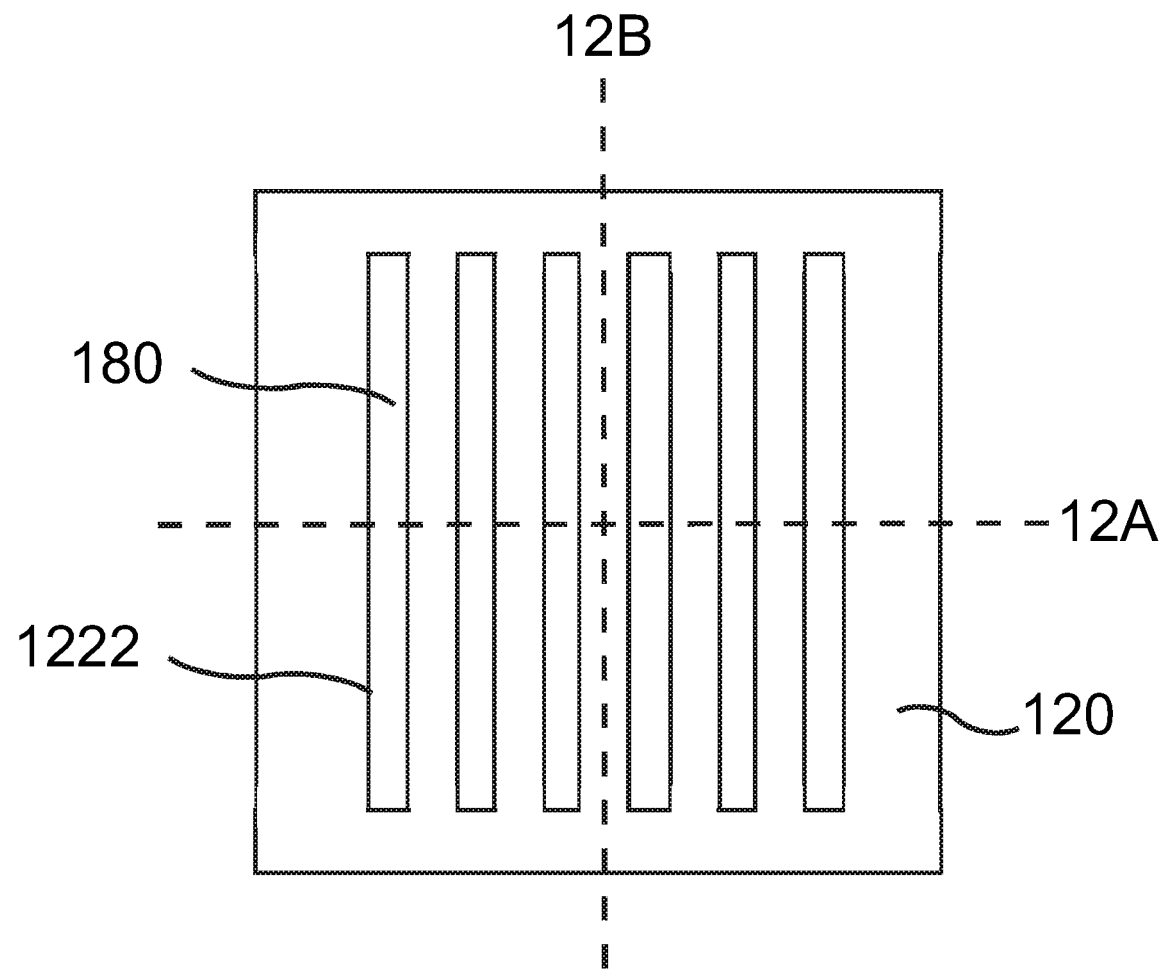
FIGS. 13A and 13B are top views illustrating multiple stages in the process of FIG. 11.
Figure 13B:
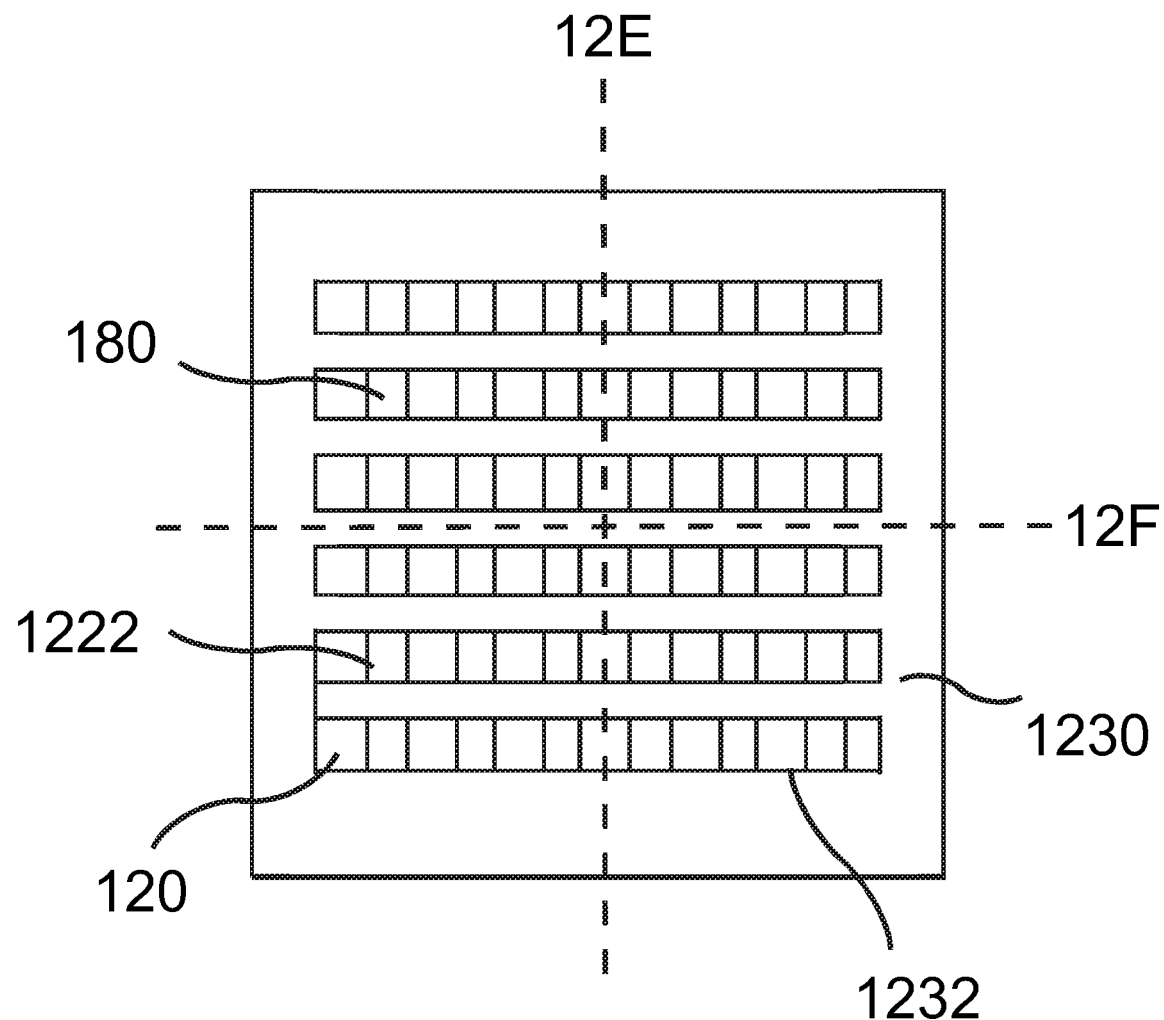
Figure 14A:
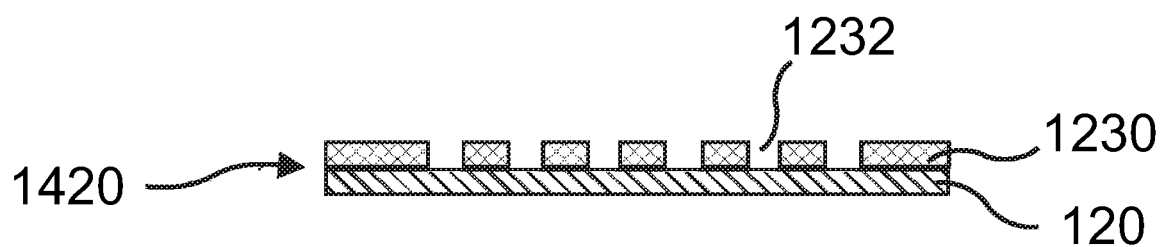
FIGS. 14A and 14B are cross-sectional views of a multi-layer microfilter 1420 in accordance with embodiments of the present invention.
Figure 14B:
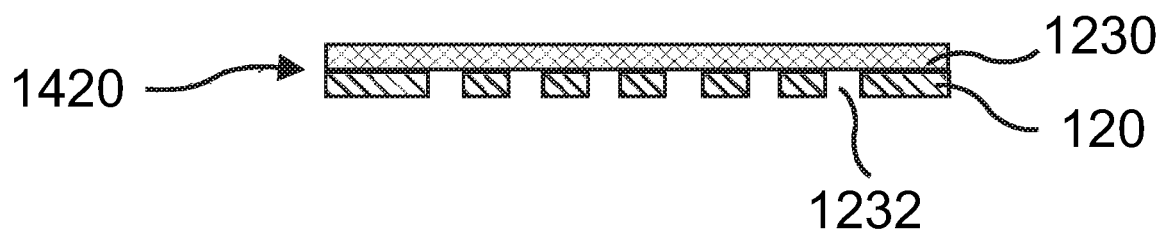
Figure 14C:
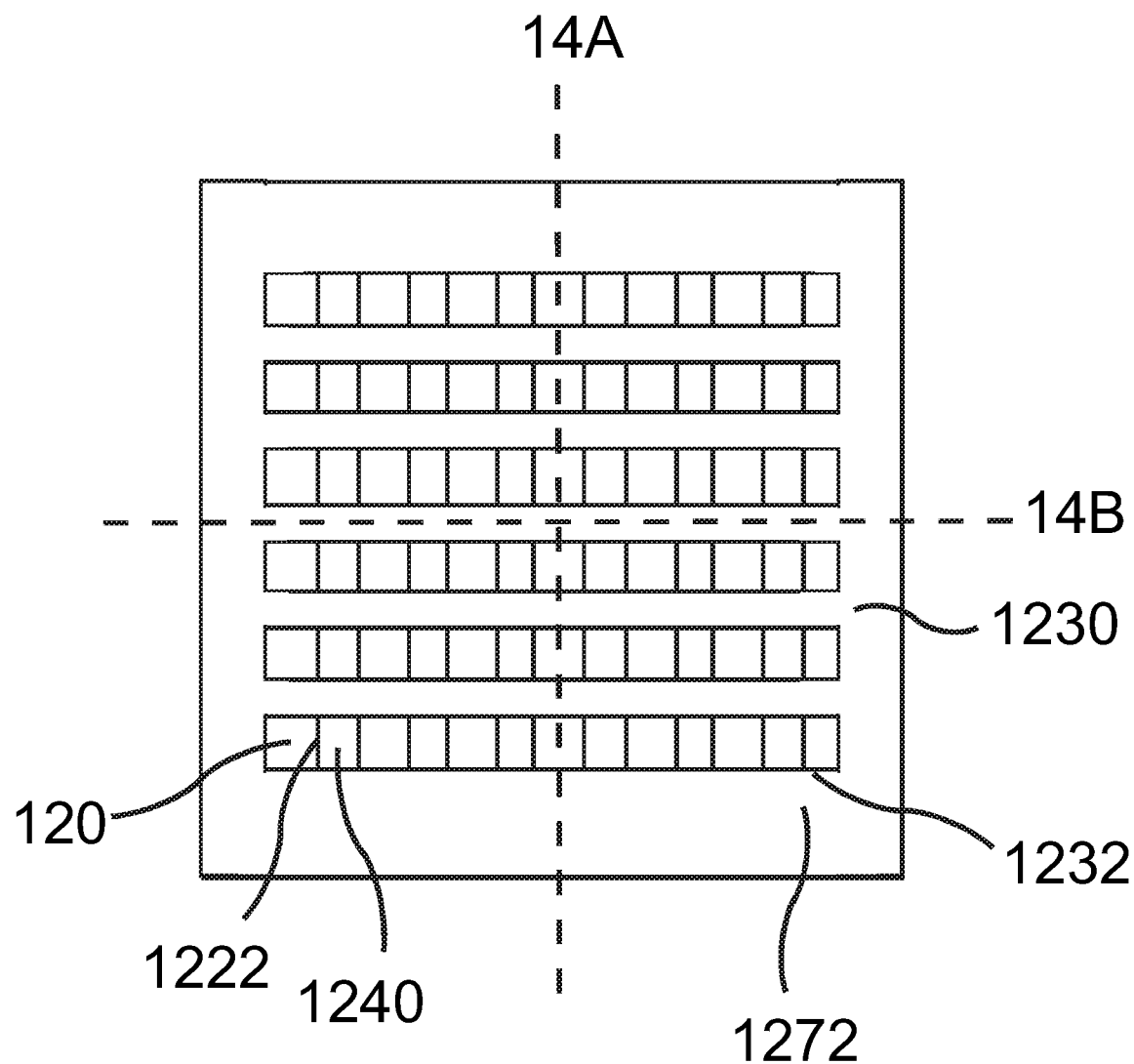
FIG. 14C is a top view of a multi-layer microfilter 1420 of FIGS. 14A and 14B.

FIGS. 12A-12K are cross-sectional views illustrating multiple stages in a process for manufacturing a multi-layer microfilter 1270 in accordance with embodiments of the present invention. FIG. 12L is a top view of multi-layer microfilter 1270 in accordance with embodiments of the present invention. FIG. 11 is a flow chart illustrating a process 1100 for manufacturing a multi-layer microfilter 1420 in accordance with embodiments of the present invention. FIGS. 14A and 14B are cross-sectional views of a multi-layer microfilter 1420 in accordance with embodiments of the present invention. FIG. 14C is a top view of a multi-layer microfilter 1420 of FIGS. 14A and 14B. The exemplary process of FIG. 11 will be described below with reference to FIGS. 12A-12F and FIGS. 14A-14C. FIGS. 13A and 13B are top views illustrating multiple stages in the process of FIG. 11.

At block 1120 of FIG. 11, a first microfilter 120 is formed on a substrate 180 from a layer of epoxy-based photo-definable dry film. In the embodiment illustrated in FIGS. 12A-12L, first microfilter 120 may be formed on substrate 180 by a process similar to the process 200 of FIG. 2A, described above, omitting the removal of microfilter 120 from substrate 180 at block 280. In certain embodiments, microfilter 120 comprises a polymer layer including a plurality of apertures. In certain embodiments of process 1100, a mask with a pattern configured for forming a plurality of elongate trenches in the dry film 100 may be used instead of mask 199 with pattern 198 configured for forming a plurality of pores in dry film 100. In such embodiments, the mask may have a pattern including elongate strips of metal so that corresponding elongate trenches may be formed in dry film 100 when dry film 100 is exposed through the mask.

FIG. 13A is a top view of microfilter 120 formed at block 1120 in accordance with embodiments of the present invention. As shown in FIG. 13A, microfilter 120 includes a plurality of elongate trenches 1222 and is disposed on a substrate 180 exposed through trenches 1222. FIG. 12A is a cross-sectional view of microfilter 120 taken along line 12A of FIG. 13A and FIG. 12B is a cross-sectional view of microfilter 120 taken along line 12B of FIG. 13A. As shown, line 12B is perpendicular to line 12A.

Figure 12C:
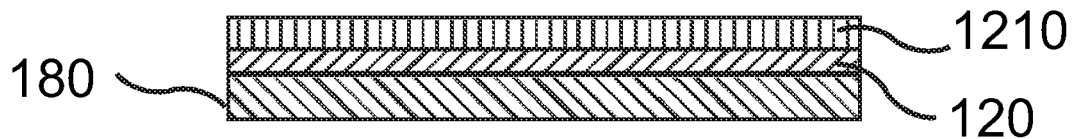
Figure 12D:
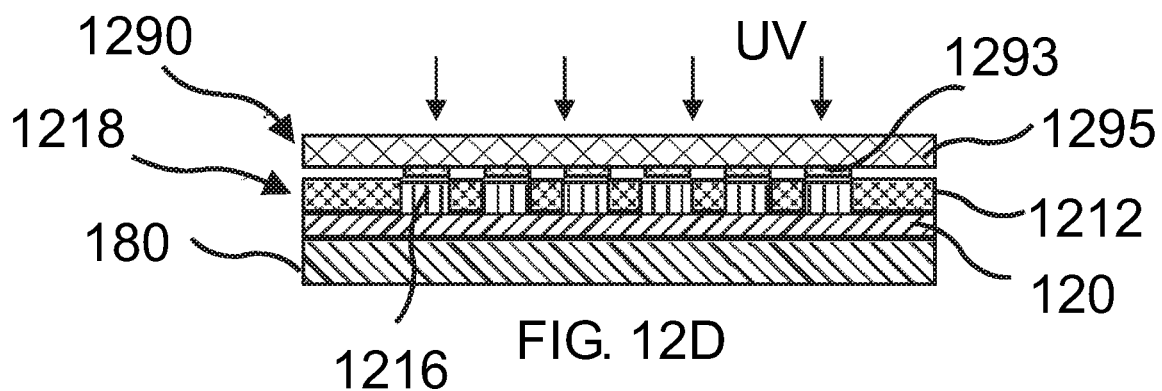

At block 1140 of FIG. 11, a layer of epoxy-based photo-definable dry film 1210 (which may be referred to herein as "dry film 1210") is laminated on microfilter 120, as shown in FIG. 12C. In certain embodiments, dry film 1210 is capable of bridging over features formed in the surface on which it is laminated. In such embodiments, dry film 1210 does not significantly fill trenches 1222 when laminated on microfilter 120. At block 1160, a second microfilter 1230 is formed from the layer of epoxy-based photo-definable dry film 1210, as described below. In certain embodiments, microfilter 1230 comprises a polymer layer including a plurality of apertures. As shown in FIG. 12D, dry film 1210 is exposed to energy through a mask 1290 to form an exposed dry film 1212 having a pattern 1218 of polymerized portions and non-polymerized portions 1216, as described above in relation to block 240 of FIG. 2A. In the embodiment illustrated in FIGS. 12A-12L, dry film 1210 is a negative resist. In other embodiments, dry film 1210 may be a positive resist and a different mask configured for use with a positive resist may be used. In the embodiment illustrated in FIGS. 12A-12L, dry film 1210 is exposed to energy in the form of ultraviolet (UV) light through an optical mask 1290 having a mask portion 1295 that is transparent to UV light and a mask pattern 1293 including a plurality of elongate strips that are opaque to UV light. In alternative embodiments, dry film 1210 may be exposed to X-rays through an X-ray mask instead of being exposed to UV light through optical mask 1290.

Figure 12E:
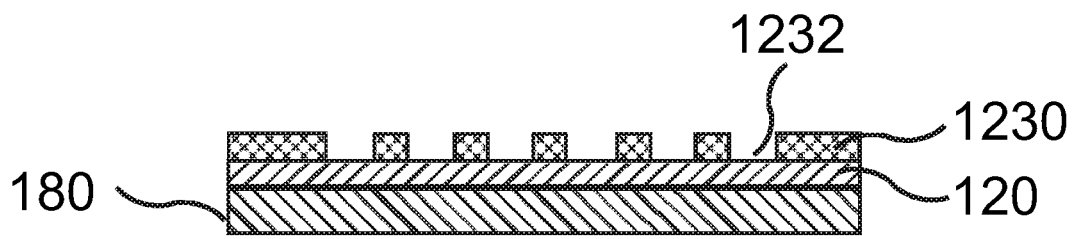
Figure 12F:
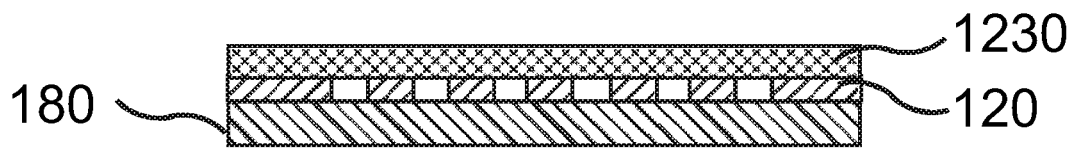
Figure 12G:
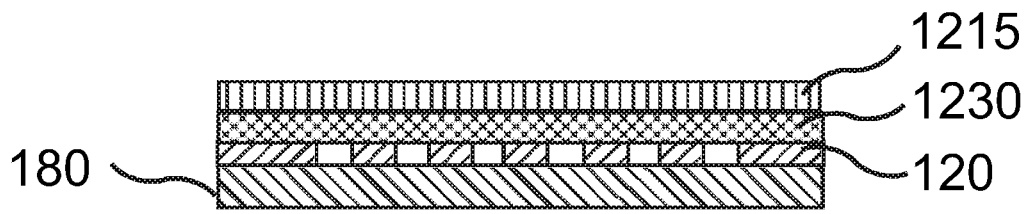
Figure 12H:
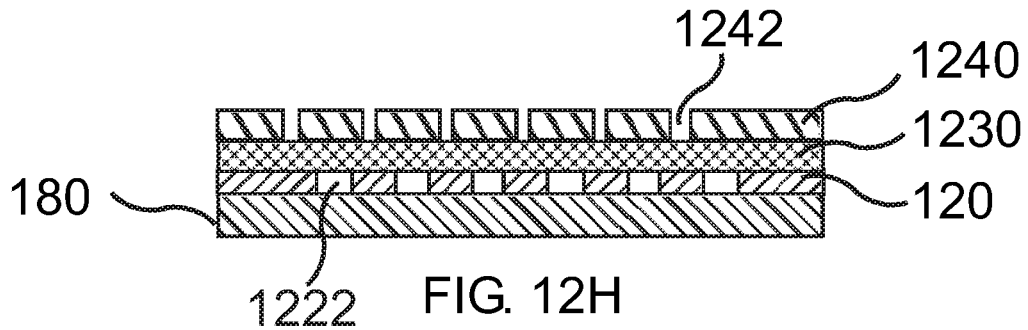
Figure 12I:
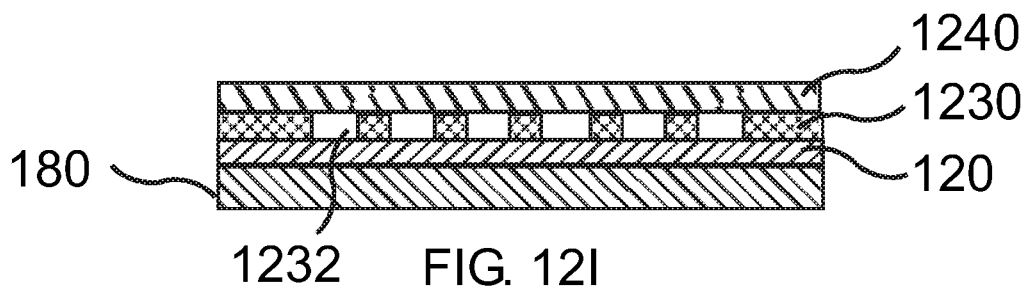
Figure 12J:
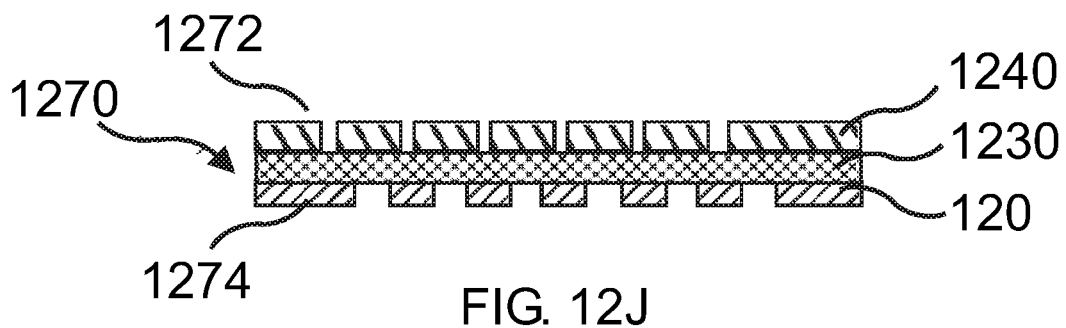
Figure 12K:
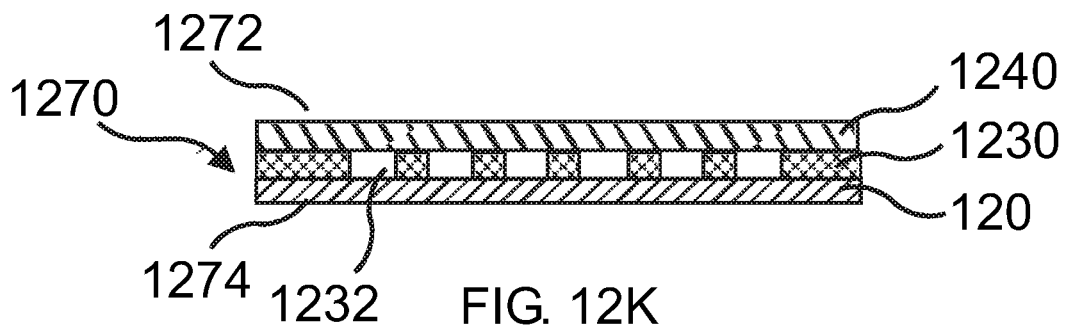
Figure 12L:
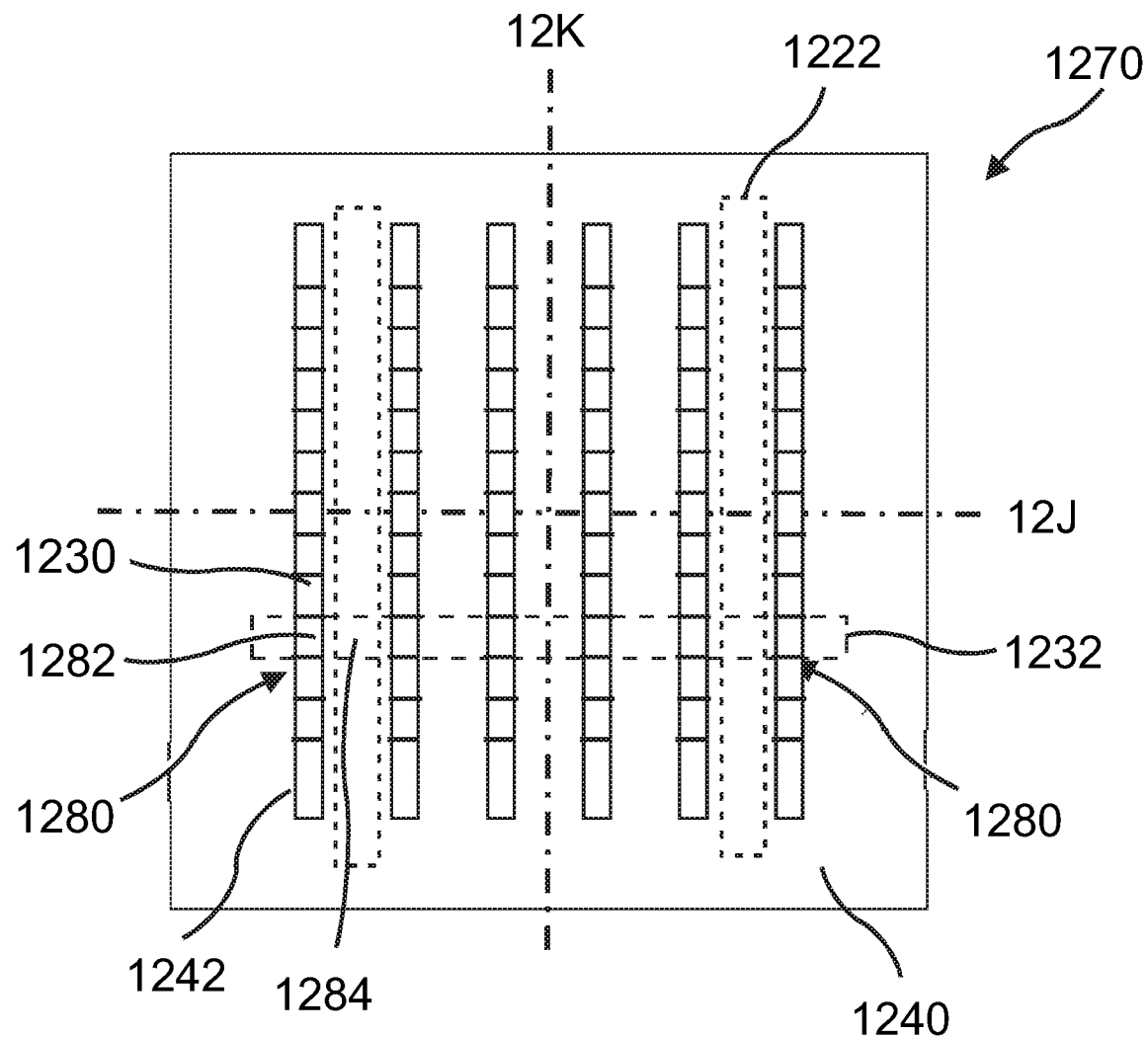
FIG. 12L is a top view of multi-layer microfilter in accordance with embodiments of the present invention.

In the embodiment illustrated in FIGS. 12A-12L, a polymeric microfilter 1230 having a plurality of trenches 1232 extending through microfilter 1230 is formed from exposed dry film 1212, as described above in relation to block 260 of FIGS. 2A and 2B, in one variation of block 1160. FIG. 13B is a top view of first and second microfilters 120 and 1230 in accordance with embodiments of the present invention. As shown in FIG. 13B, microfilter 1230 includes a plurality of elongate trenches 1232 and is disposed on first microfilter 120, which is exposed through trenches 1232. As shown in FIG. 13B, trenches 1232 of microfilter 1230 are formed substantially perpendicular to trenches 1222 of microfilter 120. FIG. 12E is a cross-sectional view of microfilters 120 and 1230 taken along line 12E of FIG. 13B, and FIG. 12F is a cross-sectional view of microfilters 120 and 1230 taken along line 12F of FIG. 13B. As shown, line 12F is perpendicular to line 12E.

In certain embodiments, after forming second microfilter 1230, substrate 180 may be removed from microfilter 120, as described above in relation to block 280 of FIG. 2A, to form a multi-layer microfilter 1420 shown in FIGS. 14A-14C. In the embodiment illustrated in FIGS. 14A-14C, multi-layer microfilter 1420 includes second microfilter 1230 disposed on first microfilter 120. As shown in FIG. 14C, multi-layer microfilter 1420 includes apertures 1240 extending through multi-layer microfilter 1420 where trenches 1222 and 1232 intersect. In certain embodiments, microfilter 1240 comprises a polymer layer including a plurality of apertures. FIG. 14A is a cross-sectional view of microfilter 1420 taken along line 14A of FIG. 14C, and FIG. 14B is a cross-sectional view of microfilter 1420 taken along line 14B of FIG. 14C. As shown, line 14B is perpendicular to line 14A.

In certain embodiments, as an alternative to forming microfilter 1420, a microfilter 1270 having a non-linear passage 1280 may be formed, as illustrated in FIGS. 12G-12L. In such embodiments, multi-layer microfilter 1270, shown in FIG. 12L, is formed by forming a third microfilter 1240 on first and second microfilters 120 and 1230 and removing substrate 180. Additionally, in such embodiments, after forming second microfilter 1230 on first microfilter 120 and substrate 180, as shown in FIG. 12F, a layer of epoxy-based photo-definable dry film 1215 is laminated on second microfilter 1230, as shown in FIG. 12G. Subsequently, third microfilter 1240 is formed from dry film 1215, as described above in relation to the formation of second microfilter 1230 and the processes of blocks 240 and 260 of FIGS. 2A and 2B. As shown in FIG. 12H, third microfilter 1240 includes a plurality of elongate trenches 1242 that are substantially perpendicular to trenches 1232 and substantially parallel with trenches 1222. Additionally, in certain embodiments, trenches 1242 are offset from trenches 1222 such that trenches 1242 are not directly above trenches 1222, as shown in FIG. 12H.

In certain embodiments, after forming third microfilter 1240, substrate 180 may be removed from microfilter 120, as described above in relation to block 280 of FIG. 2A, to form multi-layer microfilter 1270. FIG. 12L is a top view of multi-layer microfilter 1270. FIG. 12J is a cross-sectional view of multi-layer microfilter 1270 taken along line 12J of FIG. 12L, and FIG. 12K is a cross-sectional view of multi-layer microfilter 1270 taken along line 12K of FIG. 12L. As shown, line 12K is perpendicular to line 12J.

As shown in FIG. 12L, multi-layer microfilter 1270 includes non-linear passages 1280 extending through each of microfilters 1240, 1230, and 120 so as to extend from a first surface 1272 to a second surface 1274 (see FIG. 12J) of multi-layer microfilter 1270. In certain embodiments, each non-linear passage 1280 is defined by a first aperture 1282 at an intersection of trenches 1242 and 1232, a second aperture 1284 at an intersection of trenches 1232 and 1222, and a portion of trench 1232 connecting the first and second apertures. In embodiments in which a multi-layer microfilter 1270 has one or more non-linear passages 1280, the filtration path is longer than if multi-layer microfilter 1270 included only linear apertures. For clarity, only selected trenches 1232 and 1222 and selected non-linear passages are illustrated in FIG. 12L. In some embodiments, each non-linear aperture 1280 is interconnected with many other non-linear passages 1280 via trenches 1232.

In certain embodiments of the multi-layer microfilter 1270, the respective thicknesses of microfilters 120, 1230 and 1240 can be the same or different, the trenches of a microfilter may not all have the same size and/or shape, the trenches of different microfilters of the multi-layer microfilter may not all have the same size and/or shape. In some embodiments, elongate trenches 1242 may have a width of 5-7 microns and a length greater than 7 microns, wherein the length and the width are both perpendicular to the thickness of the microfilter. Alternatively or in addition, the trenches of thicknesses of microfilters may be non-linear, and the trenches of adjacent microfilters may be oriented at an angle other than 90 degrees with respect to one another. Alternatively or in addition, one or more of microfilters 120, 1230 and 1240 may include pores like any of the pores illustrated in FIGS. 9A-9D instead of trenches, and, in some embodiments, multi-layer microfilter 1270 may include more than three microfilters disposed on one another. Additionally, in certain embodiments, each of microfilters 120, 1230 and 1240 may be formed from the same type of epoxy-based photo-definable dry film.

Figure 15:
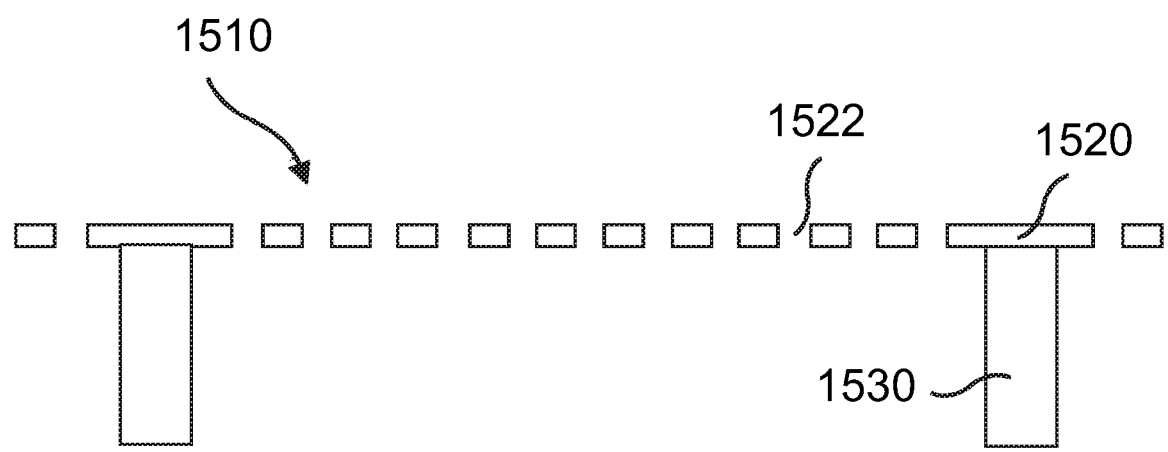
FIG. 15 is a cross-sectional view of a microfiltration structure including a microfilter and a support structure in accordance with embodiments of the present invention.

FIG. 15 is a cross-sectional view of a microfiltration structure including a microfilter and a support structure in accordance with embodiments of the present invention. In the embodiment illustrated in FIG. 15, microfiltration structure 1510 includes a microfilter 1520 having pores 1522 and disposed on a support structure 1530 configured to provide structural strength to microfilter 1520. In certain embodiments, support structure 1530 may be integrated with microfilter 1520. In some embodiments, support structure 1530 is a grid support structure. In certain embodiments, microfiltration structure 1510 may be formed by a process similar to the process described above in relation to FIGS. 12A-12F and FIGS. 14A-14C. In such embodiments, microfilter 1520 and support structure 1530 are each formed from a layer of epoxy-based photo-definable dry film and patterned using an appropriate mask. In such embodiments, microfilter 1520 is formed on support structure 1530 or support structure 1530 is formed on microfilter 1520.

In certain embodiments, surface functionalization of a polymeric microfilter may provide a surface of the microfilter with surface properties desired for a particular application of the microfilter. One technique for modifying a surface of a polymer microfilter involves performing a plasma treatment on the surface of the microfilter to activate the surface to enable chemical compounds and/or organic materials to attach to the surface. In some embodiments, another surface modification technique is to coat the microfilter with a thin layer of a metallic substance.

Figure 16:
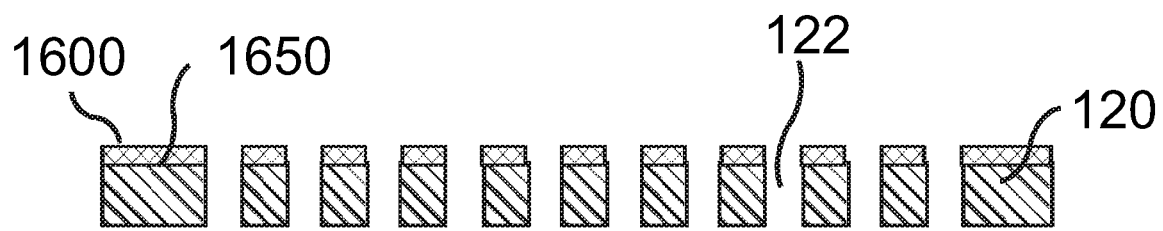
FIG. 16 is a cross-sectional view of a coated microfilter in accordance with embodiments of the present invention.

FIG. 16 is a cross-sectional view of a coated microfilter in accordance with embodiments of the present invention. Microfilter 120 is formed from a layer of epoxy-based photo-definable dry film, as described above in relation to FIGS. 1A-1E, 2A and 2B. In the embodiment illustrated in FIG. 16, microfilter 120 includes a coating 1600 on surface 1650 of microfilter 120. In certain embodiments, coating 1600 may be formed from a metallic substance, a nanoparticle colloidal substance or an organic substance. In such embodiments, these surface coatings can be used to attach analyte recognition elements, DNA, aptamers, surface blocking reagents, etc. In other embodiments, coating 1600 may include analyte recognition elements, DNA, aptamers, surface blocking reagents, etc. In certain embodiments, the surface coatings may be used to attach, for example, macromolecules such as polypeptides, nucleic acids, carbohydrates and lipids. Examples of polypeptides that may be used as analyte recognition elements include, for example, an antibody, an antigen target for an antibody analyte, a receptor (including a cell receptor), a binding protein, a ligand, or other affinity reagent to the target analyte. Examples of nucleic acids that may be used as analyte recognition elements include, for example, DNA, cDNA, or RNA of any length that allows sufficient binding specificity. In such embodiments, both polynucleotides and oligonucleotides can be used as analyte recognition elements. In other embodiments, gangliosides, aptamers, ribozymes, enzymes, antibiotics or other chemical compounds may be used as analyte recognition elements. In certain embodiments, analyte recognition coatings or elements may include, for example, biological particles such as a cell, a cell fragment, a virus, a bacteriophage or tissue. In some embodiments, analyte recognition coatings or elements may include, chemical linkers or other chemical moieties that can be attached to a waveguide and which exhibit selective binding activity toward a target analyte.

In some embodiments, coating 1600 may be formed from a metallic substance including gold, nickel, etc. In certain embodiments, coating 1600 includes gold coated on chromium. In some embodiments, it may be preferable to form coating 1600 from gold, as certain chemical compounds and organic materials readily attach to gold. In other embodiments, coating 1600 may be formed from carbon nanotubes. In the embodiment illustrated in FIG. 16, coating 1600 is disposed on one surface of microfilter 120. In other embodiments, one or more surfaces of microfilter 120 may be coated with coating 1600. In some embodiments, microfilter 120 may be completely coated with coating 1600. Coating 1600 may be disposed on one or more surfaces of any of the microfilters described herein in accordance with embodiments of the present invention, including multi-layer microfilters. In certain embodiments, coating 1600 may be disposed on one or more surfaces of multi-layer microfilter 1420. In other embodiments, coating 1600 may be disposed on one or more surfaces of multi-layer microfilter 1270.

In some embodiments, examples of chemical compounds and organic materials that may be useful for assays when deposited on the surface of a microfilter include are self-assembled monolayers with a range of functionality including amine, carboxyl, hydroxyl, epoxy, aldehyde, and polyethylene glycol (PEG) groups. These compounds and materials may be deposited on the surface of a microfilter using silane chemistry with solution immersion or vapor deposition. In certain embodiments, for example, grafting PEG-triethoxysilane onto an oxidized polymer renders the surfaces hydrophilic in a controlled manner. In other embodiments, a surface of a polymeric microfilter can be functionalized with avidin, biotin, protein A, protein G, antibodies, etc.

In certain embodiments, coating a surface of a microfilter with a metallic substance may provide other benefits in addition to facilitating the attachment of chemical compounds and/or organic materials. In some embodiments, for example, a layer of a metal metallic substance, having an appropriate thickness, can block transmission of light through the microfilter. In certain embodiments, a thickness sufficient to block the transmission of light is about 40 nm. In other embodiments, this thickness may vary depending on the substance used. Additionally, metallic substances are generally electrically conductive. In some embodiments, when the metallic substance is electrically conductive, the coating may reduce or eliminate charging of the surface of the microfilter. In alternative embodiments, a microfilter may be coated with a thin layer of PARYLENE. In other embodiments, a microfilter may be coated with a thin layer of fluorinated ethylene propylene (FEP), polytetrafluoroethylene (PTFE), perfluoroalkoxy (PFA), or another similar material. In such embodiments, coating a microfilter with one of these materials can reduce nonspecific binding; however, the fluorescent nature of these materials may make them disadvantageous when a microfilter is to be analyzed via microscope imaging.

In embodiments of the present invention described above, microfilters can be formed from epoxy-based photo-definable dry film having a thickness between 1-500 µm. In certain embodiments, such microfilters can be formed using UV light to expose the dry film (i.e., using UV lithography). In some embodiments, X-rays (i.e., X-ray lithography) may be preferred for exposing relatively thick dry films, for simultaneously exposing multiple stacked dry films, or for exposing resists that require a relatively high dose. In certain embodiments, relatively thick microfilters may provide more structural strength than thinner microfilters, but may also utilize higher pressure during filtration.

As noted above, in certain embodiments, epoxy-based photo-definable dry films are a preferred material from which to form microfilters in accordance with embodiments of the present invention. In some embodiments, properties of epoxy-based photo-definable dry film that make it a suitable material from which to form microfilters for medical diagnostic applications are that it is photo-definable by UV light, it is clear, it has a high tensile strength of 75 Mpa, it can be laminated to itself, it can be directly coated on a substrate, and it has no auto-fluorescence in the visible wavelengths. In addition, while the processes described above in accordance with embodiments of the present invention may be used to form microfilters, the processes described above may also be used to manufacture other kinds of free-standing patterned polymeric films.

Microfilters formed in accordance with embodiments of the present invention have many possible applications. In some embodiments, exemplary applications for such microfilters include medical applications, water filtration applications, beer and wine filtration applications, pathogen detection applications, etc.

Figure 17A:
FIG. 17A is a flowchart illustrating a filtration process using a microfilter in accordance with embodiments of the present invention.

FIG. 17A is a flowchart illustrating a filtration process 1700 using a microfilter in accordance with embodiments of the present invention. At block 1720 of FIG. 17A, a liquid may be passed through a microfilter formed from a layer of epoxy-based photo-definable dry film, in accordance with any one of the embodiments described above, having a plurality of apertures. In certain embodiments, the liquid may be pushed through the microfilter. In other embodiments, the liquid may be drawn through the microfilter. In some embodiments, the liquid may be passed back and forth through the microfilter one or more times. In certain embodiments, the process illustrated in FIG. 17A may be used to perform an assay using the microfilter. In certain embodiments, the process may be used to filter cells, such as CTCs, from a solution including a patient's bodily fluid. In some embodiments, filtration process 1700 may be performed with two or more filters stacked on one another with a relatively small gap between them. In such embodiments, each of the layers may have the same aperture geometries and distributions, or different aperture geometries and/or distributions.

FIG. 17B is a flowchart illustrating a filtration process 1701 using a microfilter in accordance with embodiments of the present invention. At block 1730 of FIG. 17A, a microfilter formed from a layer of epoxy-based photo-definable dry film, in accordance with any one of the embodiments described above, is positioned in a filter holder. In certain embodiments, the filter holder includes an inlet, an outlet, and securely holds the microfilter around the edges of the filter. In some embodiments, a liquid may be input into the filter holder through the outlet. At block 1750, the liquid is passed through the microfilter. In certain embodiments, the liquid is a bodily fluid or a solution including a bodily fluid. In certain embodiments, the liquid is drawn through the microfilter by applying negative pressure at the outlet of the filter holder such that all or substantially all of the liquid is drawn through the pores of the microfilter. In other embodiments, the liquid is pushed through the microfilter. At block 1770, the microfilter is removed from the filter holder. In some embodiments, the filter may then be subject to processing and or analysis to analyze any cells or other materials, substances, etc. collected by the microfilter. Exemplary applications of this process in accordance with embodiments of the present invention will be described below.

In certain embodiments, a microfilter formed from a layer of epoxy-based photo-definable dry film in accordance with any one of the embodiments described above may be used for medical diagnostics and/or prognostics. In certain embodiments, the microfilter may be used to collect certain types of cells from bodily fluids based on cell size. In some embodiments, the microfilter can be used for isolating and detecting rare cells from a biological sample containing other types of cells. In some embodiments, the microfilter can be used to filter a fluid sample, and the collected cells can be used in a downstream processes such as cell identification, enumeration (cell counting), characterization of the collected cells, culturing the collected cells, separating the cells into individual cells or groups of cells, or use the of cells in other ways. The final enriched target cells can be subjected to a variety of characterization and manipulations, such as staining, immunofluorescence of markers, cell counting, DNA, mRNA, microRNA analysis, fluorescence in-situ hybridization (FISH), immunohistochemistry, flow cytometry, immunocytochemistry, image analysis, enzymatic assays, gene expression profiling analysis, sequencing, efficacy tests of therapeutics, culturing of enriched cells, and therapeutic use of enriched rare cells. In addition, depleted plasma protein and white blood cells can be optionally recovered and subjected to other analysis, such as inflammation studies, gene expression profiling, etc.

In certain embodiments, the microfilter can be held in a filter holder for medical diagnostics and/or prognostics. In some embodiments, the filter holder may include a built in support for the microfilter. In certain embodiments, the filter holder may have gasket above and below the filter. In some embodiments, the microfilter may be used to collect circulating tumor cells (CTCs) in blood. In such embodiments, a blood sample, typically in the range of 1-10 ml, is taken from a patient. The blood sample is then drawn through the microfilter by applying negative pressure, such as a sucking force. In certain embodiments, the blood is pulled through the microfilter via an outlet. In some embodiments, passing the blood through the filter by pushing can cause cell rupture except at very low pressure or low speed.

In certain embodiments, most cells having a dimension larger than the width of one or more pores of the microfilter are retained. Most white blood cells are deformable and can pass through pores having a smaller width than a dimension of the white blood cell. In certain embodiments, nearly no red blood cells are retained on the microfilter. In some embodiments, the microfilter may include pores 7-8 μm in diameter for enriching circulating tumor cells and fetal cells; however, the microfilter pore size and shape can be varied for these applications as well.

In some embodiments, CTCs collected by the microfilter can be enumerated on the microfilter. In one experiment conducted to determine the capture efficiency of a microfilter, tumor cell lines were used. The microfilter used to demonstrate filtration efficiency was a microfilter having a 7-8 micron diameter pores separated by 20 microns and arranged within a 9 mm diameter area. The microfilter was placed into a filter holder. A prestained MCF-7 cell line was spiked into 7.5 ml of whole blood. To capture live CTCs, the blood was diluted 1:1 with a buffer solution. One exemplary buffer solution is phosphate buffered saline (PBS). The sample was drawn through the microfilter using negative pressure at approximately 10 ml/min. Afterwards, the filter was washed twice in a buffer solution. The microfilter was removed from the holder and mounted onto a microscope slide to be counted. The recovery rate of live MCF-7 cells was 85%±3%. If the blood is mildly fixed by paraformaldehyde, the capture efficiency of MCT-7 cells increases to 98%±2%.

In certain embodiments, collected CTCs can be subjected to a variety of analyses and manipulations, such as immunofluorescence, cell counting, PCR, fluorescence in-situ hybridization (FISH), immunohistochemistry, flow cytometry, immunocytochemistry, image analysis, enzymatic assays, gene expression profiling analysis, efficacy tests of therapeutics, culturing of enriched cells, and therapeutic use of enriched rare cells. In addition, in some embodiments, depleted plasma protein and white blood cells can be optionally recovered, and subjected to other analysis such as inflammation studies, gene expression profiling, etc.

In certain embodiments, a microfilter can be coated with an antibody against surface markers on the CTCs to further improve the collection of live CTCs. In some embodiments, useful antibodies may include antibodies against EpCAM, HER2, EGFR, and MUC-1, but not limited to these surface markers. In embodiments in which the microfilter is coated with an antibody as described above, the microfiltration can capture CTCs through size exclusion and using surface markers simultaneously. In such embodiments, capture efficiency of live CTCs may be improved, and the assay time for 7.5 ml of blood can be reduced from hours to minutes. In other embodiments, a microfilter formed in accordance with embodiments of the present invention is coated with tumor marker recognition reagents to collect CTCs from peripheral blood in cancer patients based on size seclusion and surface markers.

In some embodiments, captured live CTCs can be cultured directly on the microfilter to increase the number of CTCs and to evaluate the characteristics of CTCs. In other embodiments, the CTCs can be backwashed prior to culturing or sorting. In certain embodiments, the captured CTCs can be analyzed for DNA, mRNA, microRNA expressions for a target of interest to obtain genetic information. In some embodiments, the genes of CTCs can also be sequenced.

In other embodiments, a microfilter formed from a layer of epoxy-based photo-definable dry film in accordance with embodiments of the present invention may be used in therapeutic applications in which circulating tumor cells are removed from the blood of cancer patients. Circulating tumor cells are the cause of cancer spreading from the original site to other locations such as brain, lung and liver. Most carcinoma cancer patients die from the metastatic cancer. In certain embodiments, microfiltration using a microfilter formed in accordance with embodiments of the invention is a suitable method for removing circulating tumor cells from the blood stream of a patient because the filtration speed is fast and microfilters retain very little white blood cells and almost no red blood cells when used to filter blood.

Microfiltration for circulating tumor cells in blood can provide a large array of diagnostic, prognostic and research applications. For collecting circulating tumor cells, previous research reports utilized track etch filters with random pore locations with some overlapping pores and not straight pores, and microfilters with orderly arranged pores produced by reactive ion etching. In certain embodiments of the present invention, microfilters formed from epoxy-based photo-definable dry film and having precisely arranged pores are used to collect circulating tumor cells in blood.

Another exemplary application of a microfilter manufactured in accordance with embodiments of the present invention is capturing circulating fetal cells in a mother's blood during weeks 11-12 weeks of pregnancy. Such fetal cells may include primitive fetal nucleated red blood cells. Fetal cells circulating in the peripheral blood of pregnant women are a potential target for noninvasive genetic analyses. They include epithelial (trophoblastic) cells, which are 14-60 μm in diameter, larger than peripheral blood leukocytes. Enrichment of circulating fetal cells followed by genetic diagnostic can be used for noninvasive prenatal diagnosis of genetic disorders using PCR analysis of a DNA target or fluorescence in situ hybridization (FISH) analysis of genes.

Another exemplary application of a microfilter manufactured in accordance with embodiments of the present invention is collecting or enriching stromal cells, mesenchymal cells, endothelial cells, epithelial cells, stem cells, non-hematopoietic cells, etc. from a blood sample, collecting tumor or pathogenic cells in urine, and collecting tumor cells in spinal and cerebral fluids. Another exemplary application is using the microfilter to collect tumor cells in spinal fluids. Another exemplary application is using the microfilter to capture analytes bound to latex beads or antigen caused particle agglutination whereby the analyte/latex bead or agglutinated clusters are captured on the membrane surface.

Another exemplary application of a microfilter formed in accordance with embodiments of the present invention is for erythrocyte deformability testing. Red blood cells are highly flexible cells that will readily change their shape to pass through pores. In some diseases, such as sickle cell anemia, diabetes, sepsis, and some cardiovascular conditions, the cells become rigid and can no longer pass through small pores. Healthy red cells are typically 7.5 µm and will easily pass through a 3 µm pore membrane, whereas a cell with one of these disease states will not. In the deformability test, a microfilter having 5 µm apertures is used as a screening barrier. A blood sample is applied and the membrane is placed under a constant vacuum. The filtration rate of the cells is then measured, and a decreased rate of filtration suggests decreased deformability.

Another exemplary application of a microfilter formed in accordance with embodiments of the present invention is leukocyte/Red blood cell separation. Blood cell populations enriched for leukocytes (white blood cells) are often desired for use in research or therapy. Typical sources of leukocytes include whole peripheral blood, leukopheresis or apheresis product, or other less common sources, such as umbilical cord blood. Red blood cells in blood can be lysed. Then the blood is caused to flow through the microfilter with small pores to keep the leukocytes. Another exemplary application is using the microfilter for chemotaxis applications. Membranes are used in the study of white blood cell reactions to toxins, to determine the natural immunity in whole blood. Since immunity is transferable, this assay is used in the development of vaccines and drugs on white blood cells. Another exemplary application is using the microfilter for blood filtration and/or blood transfusion. In such applications, microfilters can be used to remove large emboli, platelet aggregates, and other debris.

Another exemplary application of a microfilter formed in accordance with embodiments of the present invention is using the microfilter for capturing cells and subsequently culturing the cells in the filter holder (or cartridge), or culturing the cells after backflushing the cells off the microfilter. Additionally, arrays of precision micro-pores can be fabricated in rolls of polymer resists in accordance with embodiments of the invention described above. Such arrays may be used for applications for which wafer-sized microfilters are not suitable. Examples of such applications include water filtration, kidney dialysis, etc.

While various embodiments have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents. The present embodiments are, therefore, to be considered in all respects as illustrative and not restrictive. Additionally, it will be appreciated that any features, components, elements, etc., described above in relation to different exemplary embodiments may be implemented together.

What is claimed is:

1. A microfilter comprising:
    a single polymer layer formed from an epoxy-based negative photo-definable dry film, wherein the single polymer layer has a flexibility to be disposed on a roll and unrolled; and
    a plurality of apertures formed by exposing the single polymer layer to a UV light via an optical mask to obtain a selected shape of said apertures based on said mask, each of said apertures extending through the single polymer layer having said flexibility,
    said single polymer layer having said flexibility forming a freestanding unattached microfilter structure with uniform thickness and having said flexibility.

2. The microfilter of claim 1, wherein the single polymer layer having said flexibility filters at least one type of a bodily fluid cell from a liquid comprising the at least one type of the bodily fluid cell.

3. The microfilter of claim 2, wherein the single polymer layer having said flexibility comprises a thickness, and the apertures have a width that is approximately the same as the thickness of the single polymer layer having said flexibility.

4. The microfilter of claim 1, wherein the single polymer layer having said flexibility comprises at least one surface, the microfilter further comprising:
    a coating of a metallic substance on the at least one surface of the flexible polymer layer having said flexibility.

5. The microfilter of claim 4, further comprising:
    analyte recognition elements disposed on the coating.

6. The microfilter of claim 1, wherein the single polymer layer having said flexibility comprises at least one surface, said microfilter further comprising:
    a coating of analyte recognition elements on the at least one surface of the single polymer layer having said flexibility.

7. The microfilter of claim 1, wherein the epoxy-based negative photo-definable dry film includes a polyfunctional epoxy resin.

8. A microfilter system comprising:
    a first freestanding unattached microfilter consisting of a first single polymer layer formed from a first epoxy-based negative photo-definable dry film having a plurality of first apertures formed by exposing the first single polymer layer to a UV light via an optical mask to obtain a selected shape of the first apertures based on said optical mask, each of the first apertures extending through the first single polymer layer, wherein the first single polymer layer has a flexibility to be disposed on a roll and unrolled; and
    a second freestanding unattached microfilter consisting of a second single polymer layer formed from a second epoxy-based negative photo-definable dry film and having a plurality of second apertures formed by exposing the second single polymer layer to a UV light via an optical mask to obtain a selected shape of the second apertures based on said optical mask, each of the second apertures extending through the second flexible polymer layer, wherein the second single polymer layer has said flexibility,
    at least one of the first apertures and at least one of the second apertures define at least a portion of a non-linear passage extending through the first freestanding unattached microfilter and the second freestanding unattached microfilter, wherein the first freestanding unattached microfilter and the second freestanding unattached microfilter have said flexibility.

9. The microfilter system of claim 8, further comprising:
    a third freestanding unattached microfilter consisting of a third single polymer layer formed from a third epoxy-based negative photo-definable dry film and having a plurality of third apertures formed by exposing the third single polymer layer to a UV light via an optical mask to obtain a selected shape of the third apertures based on said optical mask, each of the third apertures extending through the third single polymer layer, wherein:

the third single polymer layer has said flexibility, the at least one of the first apertures, the second aperture and third apertures define at least a portion of a non-linear passage through the first, second and third freestanding unattached microfilters, and the third freestanding unattached microfilter has said flexibility.

10. The microfilter system of claim 9, further comprising:

a coating on at least one surface of at least one of the first, second and third single polymer layers having said flexibility.

11. The microfilter system of claim 10, wherein said coating comprises analyte recognition elements.

12. A structure consisting of:

a single polymer layer formed from an epoxy-based negative photo-definable dry film, wherein the single polymer layer has a flexibility to be disposed on a roll and unrolled; and a plurality of apertures formed by exposing the single polymer layer to a UV light via an optical mask to obtain a selected shape of the plurality of apertures based on said optical mask, each of the apertures extending through the single polymer layer having said flexibility, said single flexible polymer layer having said flexibility forming a freestanding unattached microfilter with uniform thickness and having said flexibility.

13. The microfilter of claim 1, wherein said single polymer layer has a uniform thickness of 5 to 100 microns.

14. The microfilter of claim 1, wherein said single polymer layer has a uniform thickness of 10 µm.

15. The microfilter of claim 1, wherein said selected shape of said apertures is at least one of round, oval, or rectangle.

16. The microfilter of claim 1, wherein said selected shape of said apertures is round with a diameter of 7-8 µm.

17. The microfilter of claim 12, wherein said single polymer layer has a uniform thickness of 5 to 100 microns.

18. The microfilter of claim 12, wherein said single polymer layer has a uniform thickness of 10 µm.

19. The microfilter of claim 12, wherein said selected shape of said apertures is at least one of round, oval, or rectangle.

20. The microfilter of claim 12, wherein said selected shape of said apertures is round with a diameter of 7-8 µm.

* * * * *